US012779100B2

(12) United States Patent
Barnett

(10) Patent No.: US 12,779,100 B2
(45) Date of Patent: Nov. 3, 2026

(54) POLYCHROMATIC PHOTOTHERAPY DEVICE AND METHOD

(71) Applicant: Eugene Barnett, Las Vegas, NV (US)

(72) Inventor: Eugene Barnett, Las Vegas, NV (US)

( * ) Notice: Subject to any disclaimer, the term of this patent is extended or adjusted under 35 U.S.C. 154(b) by 260 days.

(21) Appl. No.: 18/797,025

(22) Filed: Aug. 7, 2024

(65) Prior Publication Data

US 2024/0390570 A1 Nov. 28, 2024

Related U.S. Application Data

(62) Division of application No. 17/172,262, filed on Feb. 10, 2021, now Pat. No. 12,083,260.

(60) Provisional application No. 62/992,447, filed on Mar. 20, 2020.

(51) Int. Cl.
*A61M 1/36* (2006.01)
*A61K 31/727* (2006.01)

(52) U.S. Cl.
CPC ......... *A61M 1/3681* (2013.01); *A61K 31/727* (2013.01); *A61M 1/3683* (2014.02); *A61M 2205/053* (2013.01)

(58) Field of Classification Search
CPC .............. A61M 1/3681; A61M 1/3683; A61M 2205/053; A61M 1/3686; A61K 31/727
See application file for complete search history.

(56) References Cited

U.S. PATENT DOCUMENTS

2014/0084179 A1* 3/2014 Ben-Hur .................. A61L 2/10 250/435
2015/0018753 A1* 1/2015 Johnson ............... A61N 5/0624 604/21
2017/0021042 A1* 1/2017 Dodd ........................ A61L 2/10

* cited by examiner

*Primary Examiner* — Kai H Weng
(74) *Attorney, Agent, or Firm* — Rockman Videbeck & O'Connor LLC

(57) ABSTRACT

A polychromatic phototherapy device for blood treatment including a casing having a triple quartz tube cuvette assembly removably installed in the casing, with blood to be treated passing through the cuvette. A plurality of light sources are mounted in the casing adjacent the cuvette to project focused light onto the blood flowing through the cuvette. The light sources include a dual wavelength UVA light source, a UVC light source, and dual wavelength red, an amber, a green and a blue LED light sources. Each of the LED light sources includes a lens assembly that projects a concentrated, highly focused linear light beam on one of the quartz tubes of the cuvette through which the blood is flowing. Once blood has been withdrawn from a patient and treated in the polychromatic phototherapy device, the blood is reinfused back into the patient.

8 Claims, 23 Drawing Sheets

| UV Dose Required for Inactivation of Microgological Issues xxxxxxxxxxxxxxxxxxxxxxxxxxxxxxxxxxxxxx | | |
|---|---|---|
| **Pathogen** | **UV Dose (mJ/cm$^2$)** | **Reference** |
| **Bacteria** | | |
| Aeromonos Hydrophillic ATCC 7966 | 5 | Wilson et al. 1992 |
| Aeromonos Salmonicida | 5.9 | Liitved & Landfald 1996 |
| Campylobacter Jejem ATCC 43429 | 4.6 | Wilson et al. 1992 |
| Citrobacter Diversus | 11.5 | Giese & Darby 2000 |
| Citrobacter Frevndil | 13 | Giese & Darby 2000(3-log) |
| Escherichia Coli ATCC 11229 | 5 | Harris et al. 1987 |
| Escherichia Coli ATCC 11303 | 10 | Wu et al. 2005 |
| Escherichia Coli ATCC 25922 | 8 | Sommer et al. 1998 |
| Escherichia Coli O157 H7 | 6 | Tosa & Hirata 1999 |
| Holobacterium Elongata ATCC 33173 | 1 | Martin et al. 2000{3-log} |
| Holobacterium Sobriorum ATCC 43214 | 20 | Martin et al. 2000 |
| Klebsiella Oneumania | 20 | Giese & Darby 2000 |
| Klebsiella Terrigena ATCC 33257 | 11 | Wilson et al. 1992 |
| Legionella Pneumaphile TCC 43660 | 9.4 | Wilson et al. 1992 |
| Solmoneba Sop. | 7 | Yuan et al. 2003 |
| Solmoneba Enteritidis | 10 | Tosa & Hirata 1998 |
| Solmoneba Infantis | 6 | Tosa & Hirata 1998{3-log} |
| Solmoneba Typhi ATCC 19430 | 8.2 | Wilson et al.1992 |
| Solmoneba Typhimunium | 50 | Maya et al. 2003 |
| Shigella Dysenteriae ATCC 29027 | 3 | Wilson et al. 1992 |
| Shigella sonaei ATCC 9290 | 8.2 | Chang et al. 1985 |
| Staphylococcus Auceus ATCC 25923 | 10.4 | Chang et al. 1985 |
| Staphylococcus Faecaiis ATCC 29212 | 11.2 | Chang et al. 1985 |

FIG. 4

| **Viruses** | | |
|---|---|---|
| PRD-1 (Phage) | 30.1 | Meng & Gerba 1996 |
| B40-8 (Phage) | 28 | Sommer et al. 2001 |
| MS2 (Phage) | 83 | Nieuwstad & Havelarr 1994 |
| Calicivirus Canine | 30 | Husma et al. 2004 |
| Calicivirus Feline | 25 | Iree et al . 2005 |
| Adenovirus Type 2 | 100 | Ballester & Malley 2004 |
| Adenovirus Type 15 | 165 | Thompson et al. 2003 |
| Adenovirus Type 40 | 155 | Thurston-Enriquez et al. 2004 |
| Adenovirus Type 41 | 111.8 | Meng & Gerba 1996 |
| Poliovirus 1 | 27 | Tree et al. 1987 |
| Coxsackievirus B3 | 32.5 | Gerba et al. 2002 |
| Coxsackievirus B5 | 36 | Gerba et al. 2002 |
| Reovirus 3 | 22.4 | Rauth 1965 |

FIG. 5

Ozone or Oxygen May be Mixed with Blood

POLYCHROMATIC PHOTOTHERAPY DEVICE AND METHOD

CROSS-REFERENCE TO RELATED APPLICATION(S)

This application claims priority to U.S. provisional patent application Ser. No. 62/992,447, filed on Mar. 20, 2020, and claims priority to and is a divisional of non-provisional patent application Ser. No. 17/172,262, filed on Feb. 10, 2021, to the extent allowed by law.

TECHNICAL FIELD

This disclosure relates to a polychromatic phototherapy device and method and, more particularly, to a photoluminescence blood treatment unit and method.

BACKGROUND

Many illnesses develop from the body's inability to buffer free radicals through inadequate intracellular proteins. The application of oxidative and light therapy in measured doses restores the body's ability to buffer free radicals, activate immune function, and correct cellular metabolism. Once blood, treated with oxidative and light therapy, is reintroduced into the body, that treated blood delivers small doses of light energy into the body and the immune system receives a blueprint of destroyed pathogens which it analyzes and subsequently produces antibodies for. Ultraviolet light exposure to the blood and its components can result in damage to the DNA of pathogens, killing them and/or rendering them unable to replicate, thereby resulting in an autogenous "vaccine"-like effect in the blood. The ultraviolet blood irradiation promotes the coagulation of bacteria by creation of an autogenous vaccine, increases the germicidal properties of blood, and increases the number of antibodies in the body.

SUMMARY

This disclosure relates generally to a polychromatic phototherapy device and method. Multiple sources of UV and LED light are applied to blood passing through a cuvette located adjacent to the light sources. The high energy light sources emit dual wavelengths in the UVA range and the UVC range, and further photonic energy is generated from 60 watts of highly focused LED light sources in the visible spectrum. Each light source has been shown to have specific biological benefits. Each LED light source is enclosed in an individual focusing lens assembly.

These and other aspects of the present disclosure are disclosed in the following detailed description of the embodiments, the appended claims and the accompanying figures.

BRIEF DESCRIPTION OF THE DRAWINGS

The various features, advantages, and other uses of the apparatus will become more apparent by referring to the following detailed description and drawings, wherein like reference numerals refer to like parts throughout the several views. It is emphasized that, according to common practice, the various features of the drawings are not to-scale. On the contrary, the dimensions of the various features are arbitrarily expanded or reduced for clarity.

FIG. 4 is a chart of ultraviolet dose required for inactivation of microbiological pathogens ;

FIG. 5 is a chart of ultraviolet dose required for inactivation of viral bodies;

DETAILED DESCRIPTION

Many illnesses develop from the body's inability to buffer free radicals through inadequate intracellular proteins. The application of oxidative and light therapy in measured doses restores the body's ability to buffer free radicals, activate immune function, and correct cellular metabolism. Once blood, treated with oxidative and light therapy, is reintroduced into the body, that treated blood delivers small doses of light energy into the body and the immune system receives a blueprint of destroyed pathogens which it analyzes and subsequently produces antibodies for. Ultraviolet light exposure to the blood and its components can result in damage to the DNA of pathogens, killing them and/or rendering them unable to replicate, thereby resulting in an autogenous "vaccine"-like effect in the blood. The autogenous vaccine-like effect is produced when the primary blood treated by ultraviolet light is reintroduced back into the body, the primary blood carries the photonic light energy to the untreated portion of the blood in the body, inducing secondary radiation that is subsequently emitted. The ultraviolet blood irradiation promotes the coagulation of bacteria by creation of an autogenous vaccine, increases the germicidal properties of blood, and increases the number of antibodies in the body.

Phototherapy comprises oxidation and irradiation of the blood providing improved microcirculation and oxygenation of tissues, anti-inflammatory effects, stimulation of the immune system, increased tolerance of the body towards radiation and/or chemotherapy, cardiovascular protection through increased metabolism of cholesterol, uric acid, and glucose, resolution of vascular spasms, and powerful anti-infection properties. Mitochondria are thought to be a likely site for the initial effects of light, leading to increased adenosine triphosphate (ATP) production, modulation of reactive oxygen species, and induction of transcription factors. These effects, in turn, lead to increased cell proliferation and migration, particularly by fibroblasts, modulation in levels of cytokines, growth factors and inflammatory mediators, and increased tissue oxygenation.

Figure 1:
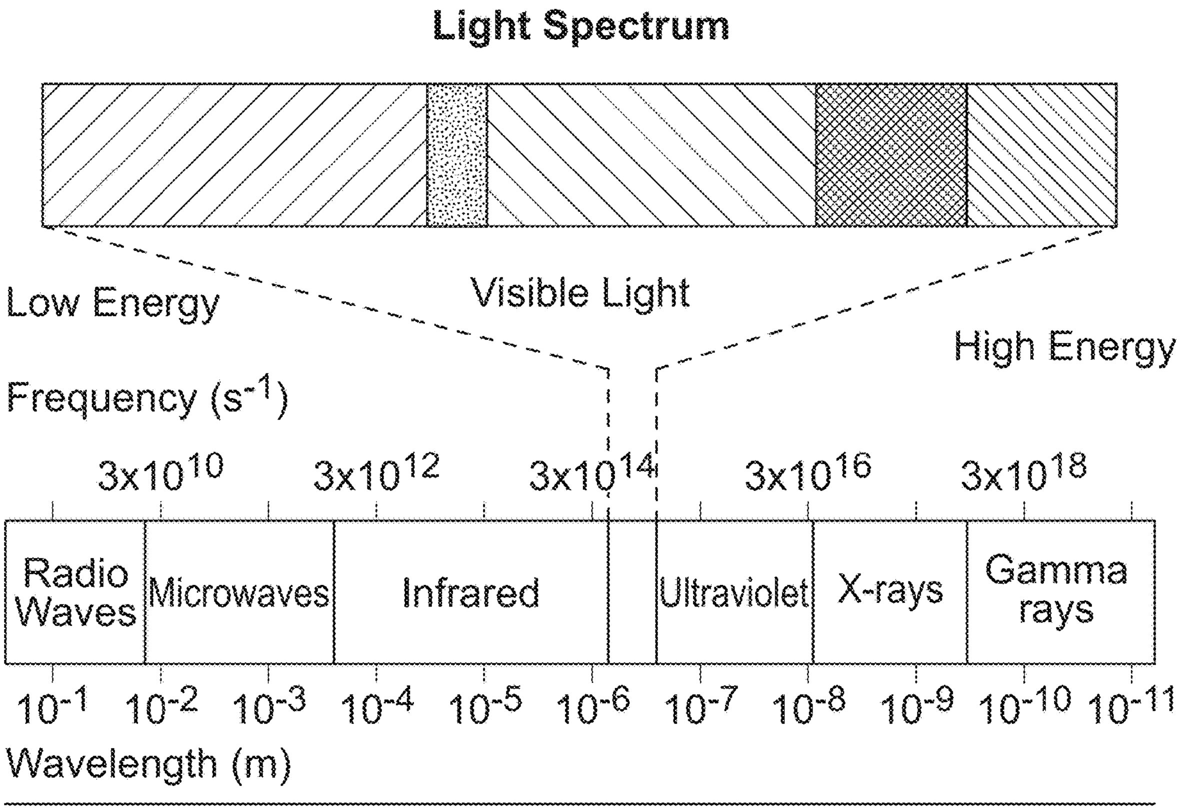
FIG. 1 is a diagram of the light spectrum wavelengths.
Figure 3:
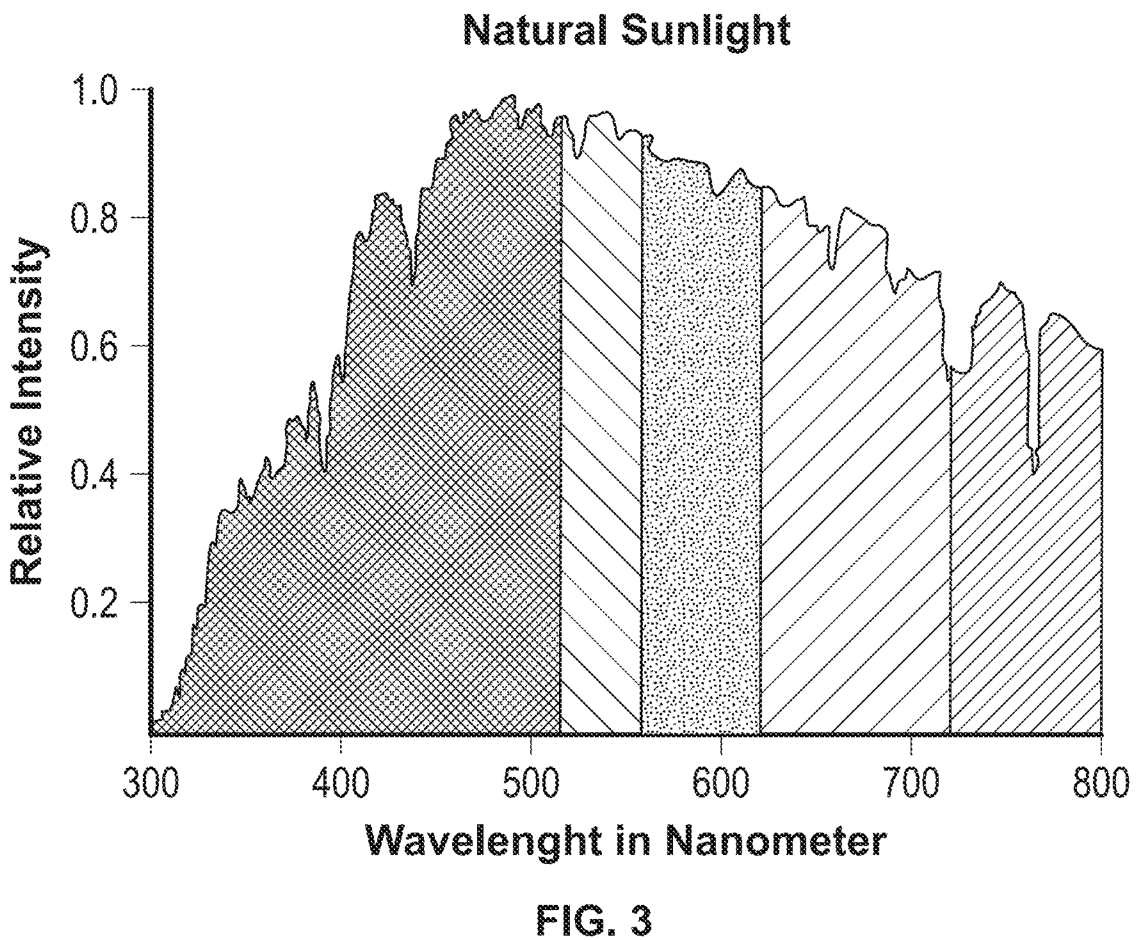
FIG. 3 is a chart of natural sunlight regarding relative intensity as to wavelength.

Ultraviolet (UV) radiation is part of the electromagnetic spectrum, shown in FIG. 1, with a wavelength range of 100-400 nm, that is shorter than that of visible light, which has a wavelength range of 400-700 nm, but is longer than that of x-rays, which have a wavelength range less than 100 nm. UV radiation is divided into four distinct spectral areas, which include vacuum UV (100-200 nm), UVC (200-280 nm), UVB (280-315 nm), and UVA (315-400 nm). UV light in its multiple wavelengths comprises approximately 10% of sunlight, as shown in FIG. 3.

Figure 2A:
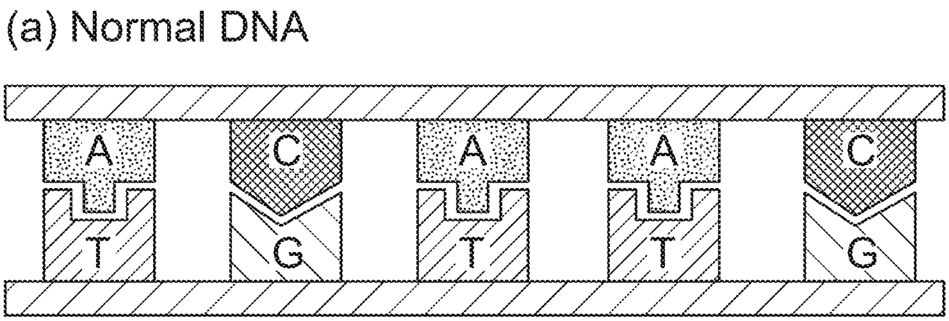
FIG. 2A is a diagram of normal DNA, prior to ultraviolet light exposure.
Figure 2B:
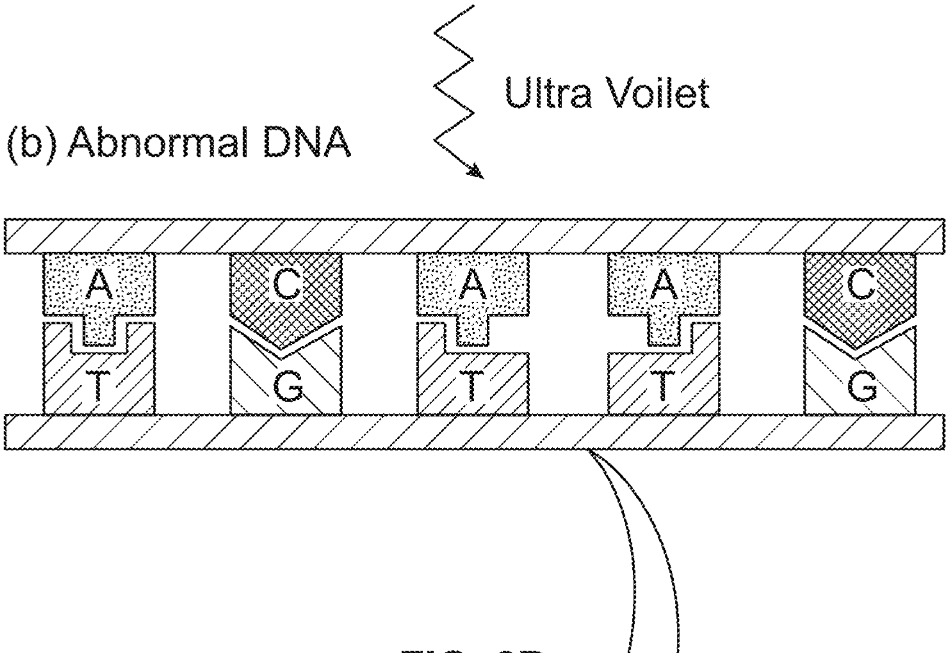
FIG. 2B is a diagram of abnormal DNA, after ultraviolet light exposure.
Figure 2C:
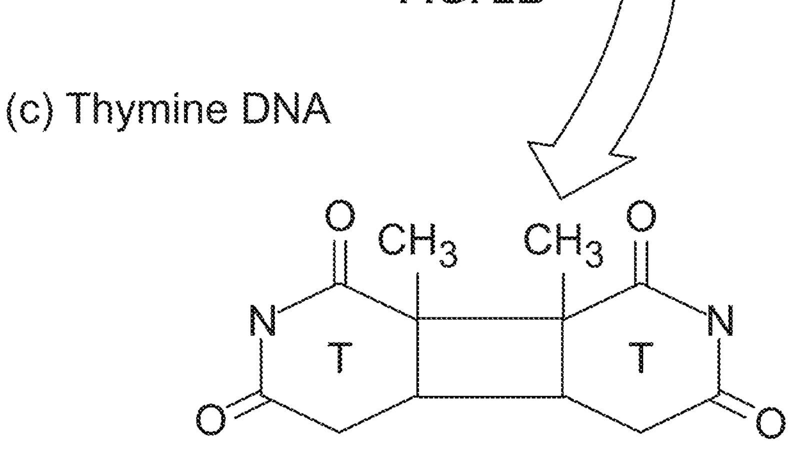
FIG. 2C is a diagram of thymine dimer produced by ultraviolet light exposure.

Ultraviolet (UV) light is very effective in disabling bacteria and viruses by damaging their DNA. Normal DNA is shown in FIG. 2A while DNA damaged by UV light is shown in FIG. 2B. The UV light causes numerous cytosine and thymine bases to form covalent bonds with themselves and each other, producing dimers, mainly thymine-thymine dimers as shown in FIG. 2C, which makes it difficult for enzymes to make proper copies of DNA. The enzymes will either completely skip such areas without adding a complementary base or add one at random that may well be the wrong one, which produces serious metabolic problems thereby killing the pathogen.

When microorganisms are subjected to UV light, cellular DNA absorbs the energy by purines and pyrimidine bases, causing adjacent thymine molecules to link together. Linked thymine molecules are unable to encode adenine on messenger RNA molecules during the process of protein synthesis. Moreover, replication of the chromosome in binary fission is impaired. The damaged organism can no longer produce critical proteins or reproduce, causing the organism to quickly die. UV light is especially effective in killing viruses. However, UV light kills far fewer bacteria than one might expect because of the bacteria's DNA repair mechanisms. Once DNA is repaired, new molecules of RNA and protein can be synthesized to replace the damaged molecules. Viral bodies generally require more energy to deactivate or kill than pathogens, as shown in FIGS. 4 and 5.

A polychromatic phototherapy device of the present disclosure comprises multiple elements which are designed to work synergistically in the treatment of auto-immune, viral, bacterial, fungal, and terminal diseases with a minimally invasive photoluminescence blood treatment unit specifically designed to safely expose a small portion of a patient's blood through precisely controlled exposure to a full spectrum of light, including wavelengths known to increase immune response. The polychromatic phototherapy device is designed to deliver a significant amount of wide spectrum photonic energy over a prolonged period of time via an energetic photonic infusion of the blood.

The polychromatic phototherapy device utilizes multiple light sources, including enhanced spectrum, high energy light sources emitting wavelengths from 253.7 00 nm (UVC light) to 685 nm which is well into the visible light range. The polychromatic phototherapy device is equipped with both a high power dual wavelength UVA light source and a high output UVC light source. Further photonic energy is generated from 60 watts of highly focused, high power LEDs, whose emitted energy is in the visible spectrum. The combined UV sources deactivate the DNA of bacteria, viruses, and other pathogens, thereby destroying their ability to multiply and cause disease. The polychromatic phototherapy device enables the medical community to treat chronic conditions, as well as acute conditions, including Dengue, Zika, HIV, Coronavirus 19, septicemia, and snake and spider bites.

Additionally, the principle behind the triple UV light emission architecture of the polychromatic phototherapy device of the present disclosure is based in the Krebs Cycle and is designed to propel and promote energetic ability to increase the mitochondrial electron transfer. The device 10 (FIG. 9) accomplishes this by providing peak energy absorption spectrums unique to both NAD+ and NADH. Nicotinamide adenine dinucleotide is involved in redox reactions, carrying electrons from one reaction to another. The coenzyme is, therefore, found in two forms in cells. NAD+ is an oxidizing agent that accepts electrons from other molecules and becomes reduced. This reaction forms NADH, which can then be used as a reducing agent to donate electrons. These electron transfer reactions are the main function of NAD. However, NAD is also used in other cellular processes, the most notable one being a substrate of enzymes that add or remove chemical groups from proteins in post-translational modifications.

Blood treated with the polychromatic phototherapy device facilitates the following: renders virus and bacteria unable to replicate; increases the capabilities for oxygenation, by activating the 2, 3, DPG enzyme system, which potentiates oxygen from the heme complex into the tissues; enhances mitochondrial energy deficiencies; stimulates lymphatic detoxification by restoration of functional chylomicron Brownian movement within the blood; activates immune cells, such as NK cells, neutrophils, and macrophages, and assists in the balancing of cytokine production, which activation aids in the destruction of various microorganisms, fungi, viruses, and bacteria; activates NAD+; dismantles nagalese, which is a protein produced principally by cancer, viruses, and some bacterium and disables the glycoprotein which is the basis for the body producing GCMAF, which is also a glycoprotein which binds to the macrophage and acts as a switch to turn on the macrophage function; activates many other cytotoxic immune cells such as NK cells; and influences Zeta potential, which refers to the free flowing components of red blood cells (RBC).

Figure 6:
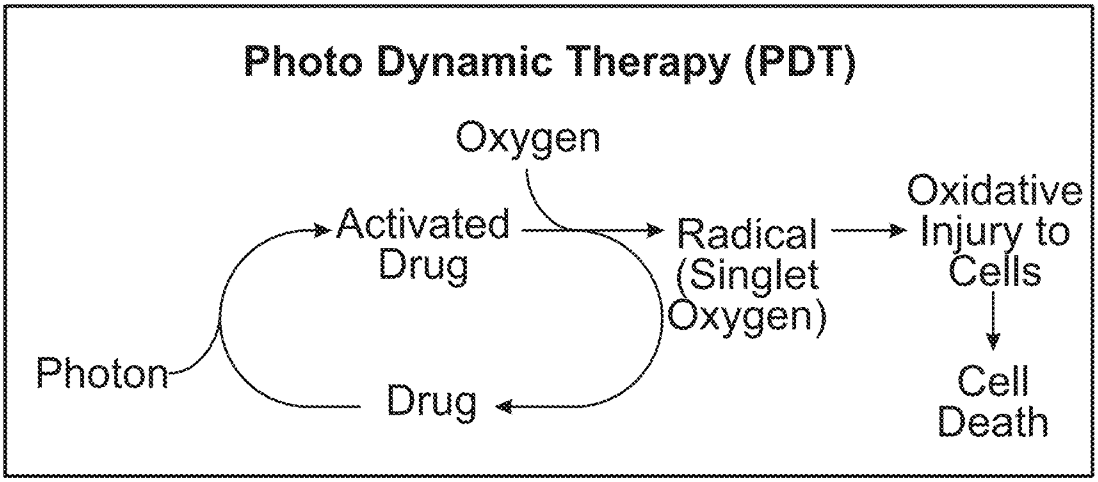
FIG. 6 is a chart showing photodynamic therapy.

Referring to FIGS. 9-13B, a first embodiment of a polychromatic phototherapy device 10 of the present disclosure is shown. The polychromatic phototherapy device 10 utilizes eight primary wavelengths in the process of deactivating pathogens while up regulating immune response, increasing nitric oxide (NO), balancing redox, improving blood flow, and enabling simultaneous photodynamic therapy, as shown diagrammatically in FIG. 6. The presently disclosed device uses eight primary wavelengths of light to deactivate blood borne pathogens. These light sources also have the capacity to simultaneously, or solely, photoactivate photo-sensitive substances that subsequently absorb electrons and act as electron donors in the process of photoinactivation of pathogens.

Figure 9:
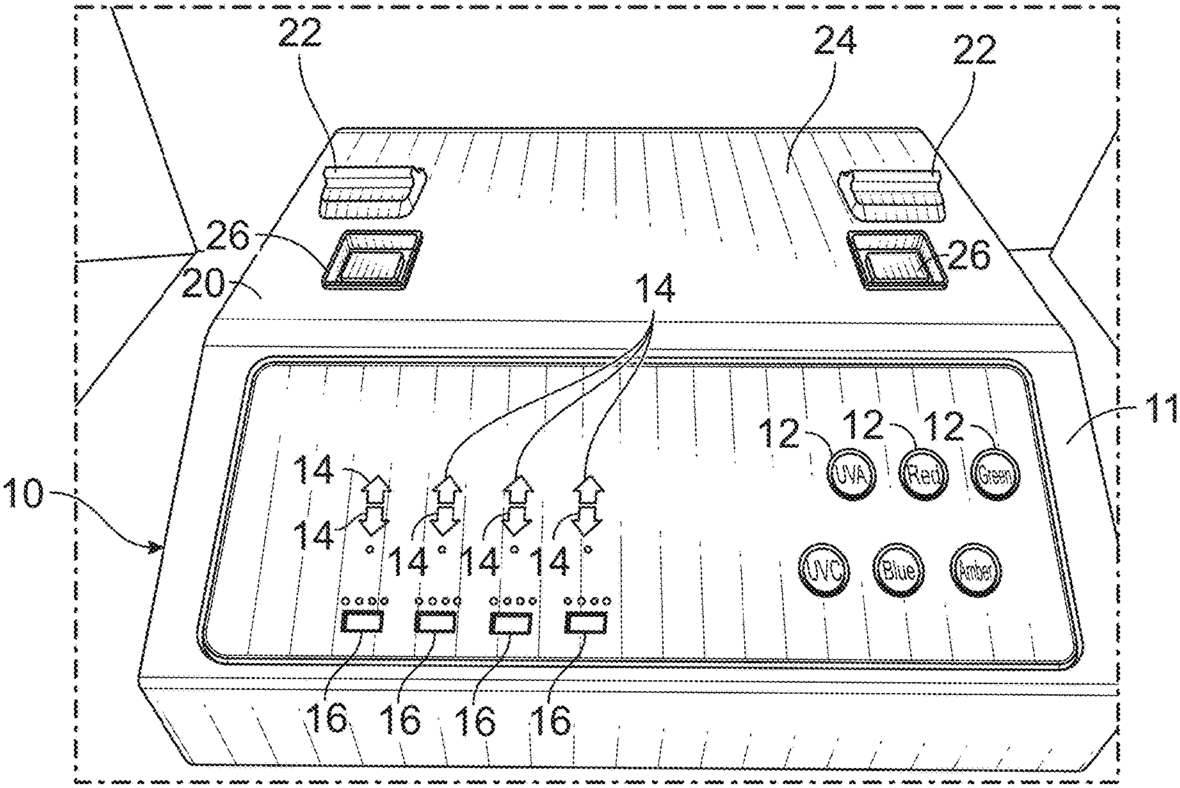
FIG. 9 is a front perspective view of the housing for the first embodiment of the polychromatic phototherapy device in accordance with implementations of this disclosure.
Figure 17:
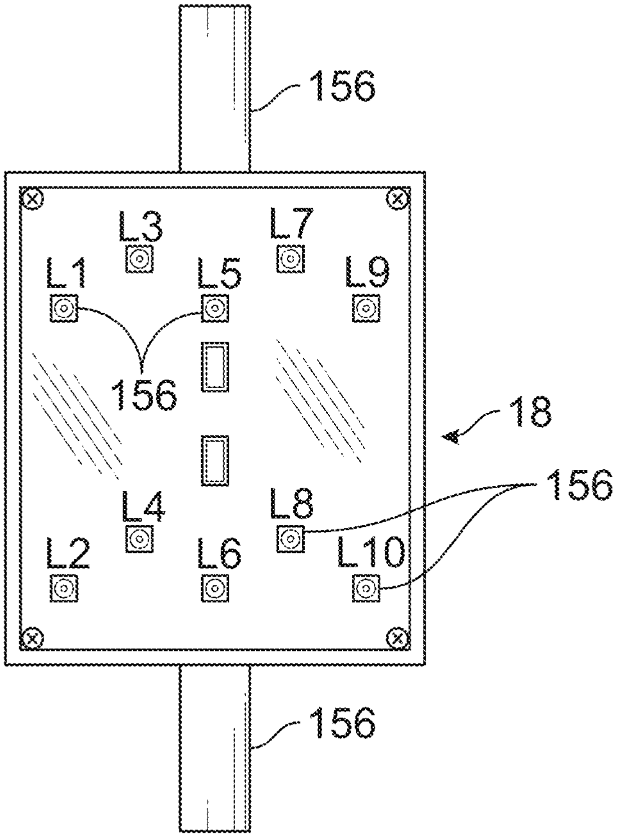
FIG. 17 is a front view of one of the wrist pads shown in FIG. 16.

Referring to FIG. 9, the polychromatic phototherapy device 10 comprises six independently controlled light source switches 12, intensity dome switches 14, and USB ports 16. The six independently controlled light sources, in this illustrated embodiment, as described in detail below, include a UVA light source, a UVC light source, two double wavelength red LED light assembly strips, two LED amber light assembly strips, one blue LED light assembly strip, and one LED green light assembly strip. Switches 12 are independent controls to turn on and turn off the individual light sources, providing the operator with full control of the blood treatment. The polychromatic phototherapy device 10 can also include two high optical density double wavelength photo red/I.R. wrist pads 18, as shown in FIG. 17, connected to the device 10 through the USB ports 16, that provide optional photodynamic therapy treatment via the radial artery and the ulnar artery (FIG. 7), which have significant blood flow and are relatively shallow and easy to access, when used with photo-active substances described above.

Housing 11 of device 10 includes a pivotal access panel 20 attached by hinges 22 to stationary panel 24 forming the rear of housing 11. Finger operated latches 26 hold access panel 20 in a closed position until the operator lifts latches 26. Panel 24 is then rotated upward, providing manual and visual access to the light and to the triple quartz tube cuvette assembly 66 (FIGS. 10-16) disposed in the interior space of housing 11.

The intensity of the wrist pads 18 are controlled by the four intensity dome switches 14, located above the USB ports 16, which allow the user to increase and/or decrease the intensity of the deep red/photored LED lights emitted by the wrist pads 20. Deep red/photored LED lights are densely populated when applied to the wrist area to promote the photodynamic therapy treatment, increase circulation, and activate liposomal methylene blue, with added deoxycholic acid and minerals, if used, when administered, either orally or by I.V. infusion, 20 to 30 minutes prior to the treatment with the device 10. The photodynamic therapy treatment can also be administered during or after the polychromatic phototherapy treatment with the device 10.

Photodynamic therapy utilizes the administration of any of six photo activated sensitizers or photo-active substances: PAS 1, 2, 3, 4, 5, 6, and 7; psoralen drugs, 8-MOP, porphyrins, chlorins, and liposomal methylene blue. Photodynamic therapy can produce a number of side effects, including increased light sensitivity, "collateral damage" to healthy cells due to a lack of specificity, fatigue, Herkshemier reaction, fever, and/or chills. Photoluminescent therapy comprises four parameters: the amount of blood taken from the patient; time of exposure of the blood to the light; the intensity and the wavelengths of the spectral energy used; and the sensitivity of the photo-active drug, if used in the therapy.

Figure 10:
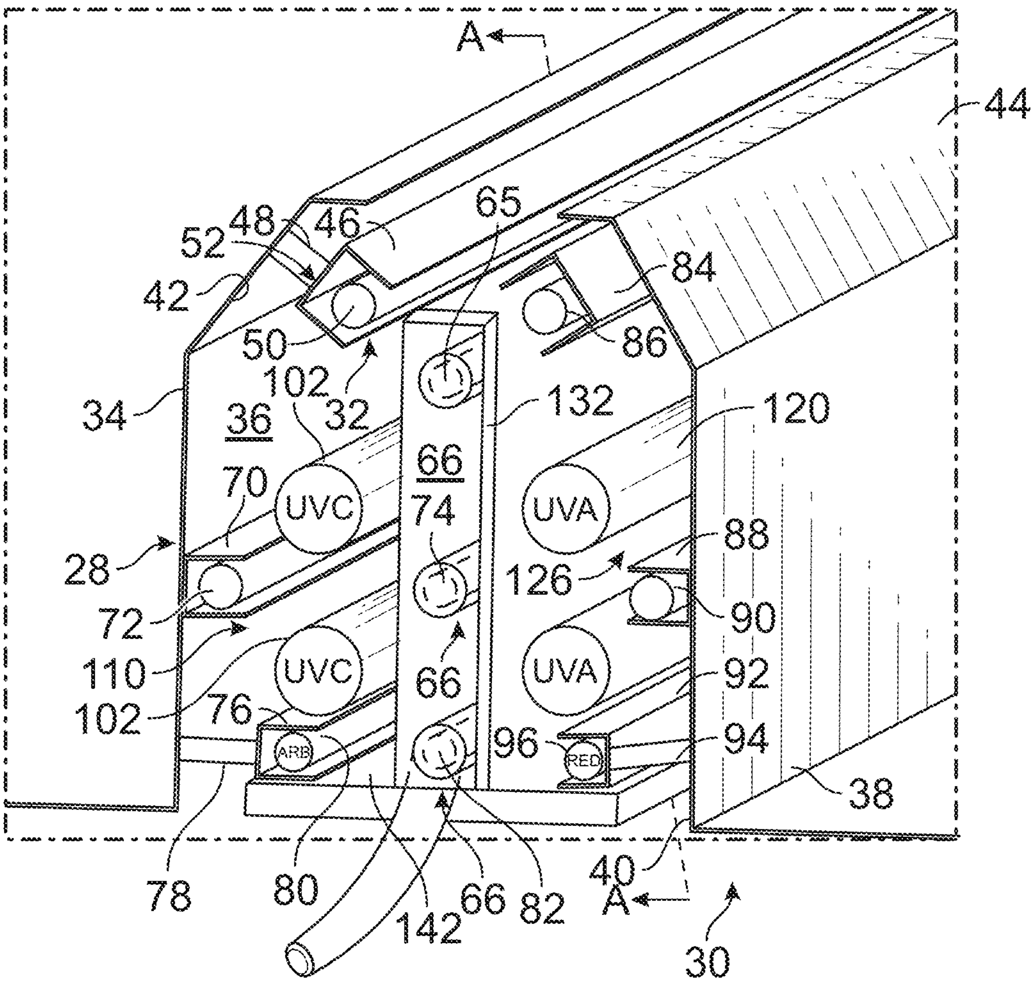
FIG. 10 is a partial perspective schematic view of the front and rear light assemblies located inside the housing of FIG. 9.
Figure 11:
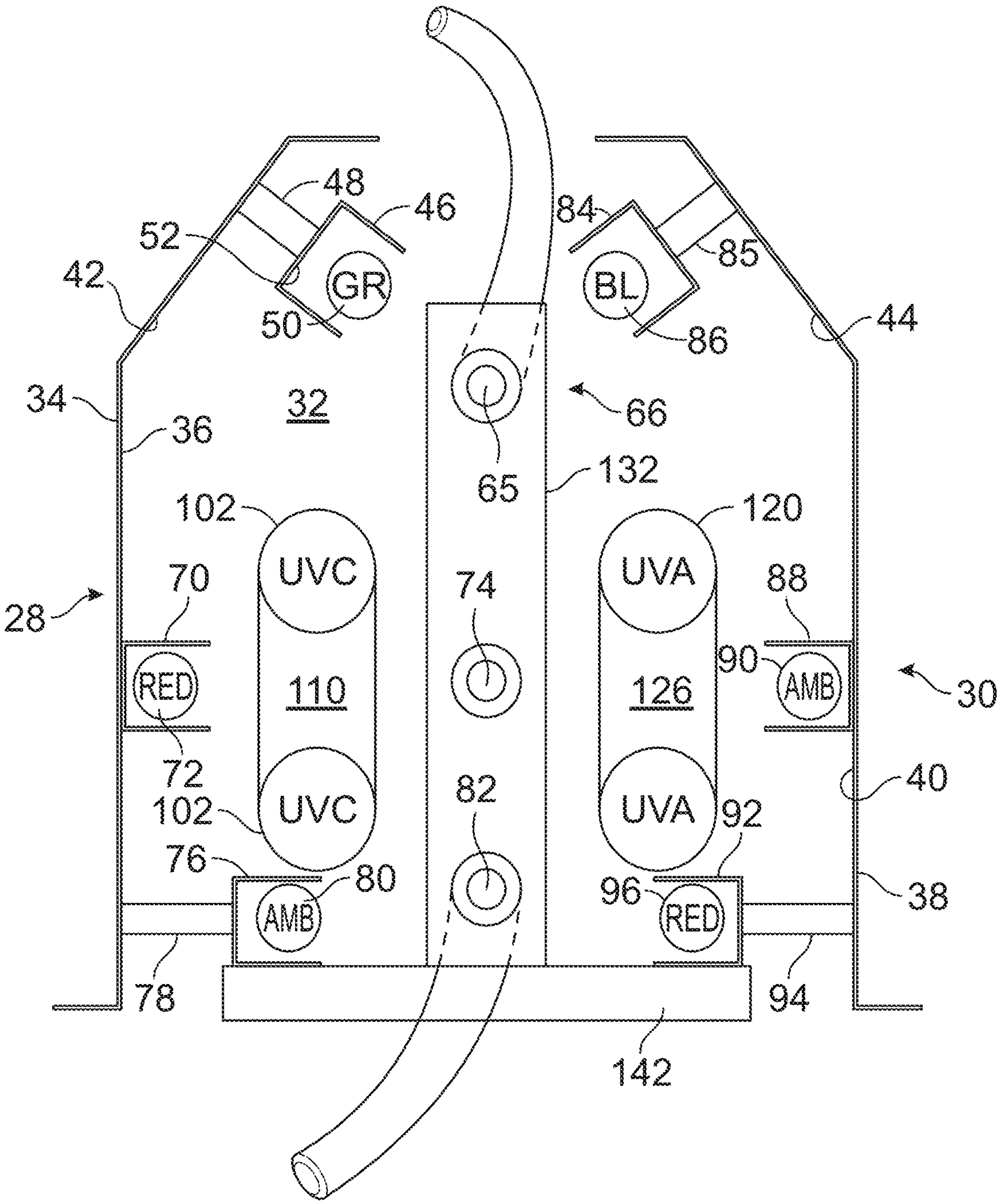
FIG. 11 is a cross section schematic view of the front and rear light assemblies taken along line A-A of FIG. 10.

Referring to FIGS. 10 and 11, the interior of housing 11 of device 10 includes a front light assembly 28 and a rear light assembly 30, with a space forming treatment chamber 32 between the two light assemblies. Front light assembly 28 comprises a front light support panel 34 having a reflective surface 36 facing inward toward treatment chamber 32. Rear light assembly 30 comprises a rear light support panel 38 having a reflective surface 40 facing inward towards treatment chamber 32. Front light support panel 34 includes an angled portion 42, and rear light support panel includes an angled portion 44.

A first substantially U-shaped LED light housing 46 is attached by a plurality of supports 48 to the interior reflective surface 36 of front light assembly 28. Mounted in the channel formed in first LED light housing 46 is a green LED light assembly strip 50 extending substantially the horizontal length of first LED light housing 46. Due to the angle of angled portion 42 of front light support panel 34, and the lens assembly (FIG. 13A) included in green LED light assembly strip 50, the light emitted by the green LED lights in assembly strip 50 is finely focused and directed downward at an angle towards a specific linear location in chamber 32, for a purpose to be explained. The green light emitted from green LED light assembly strip 50 is optimally 525 nm, but could be in the range of 510-540 nm.

Figure 12:
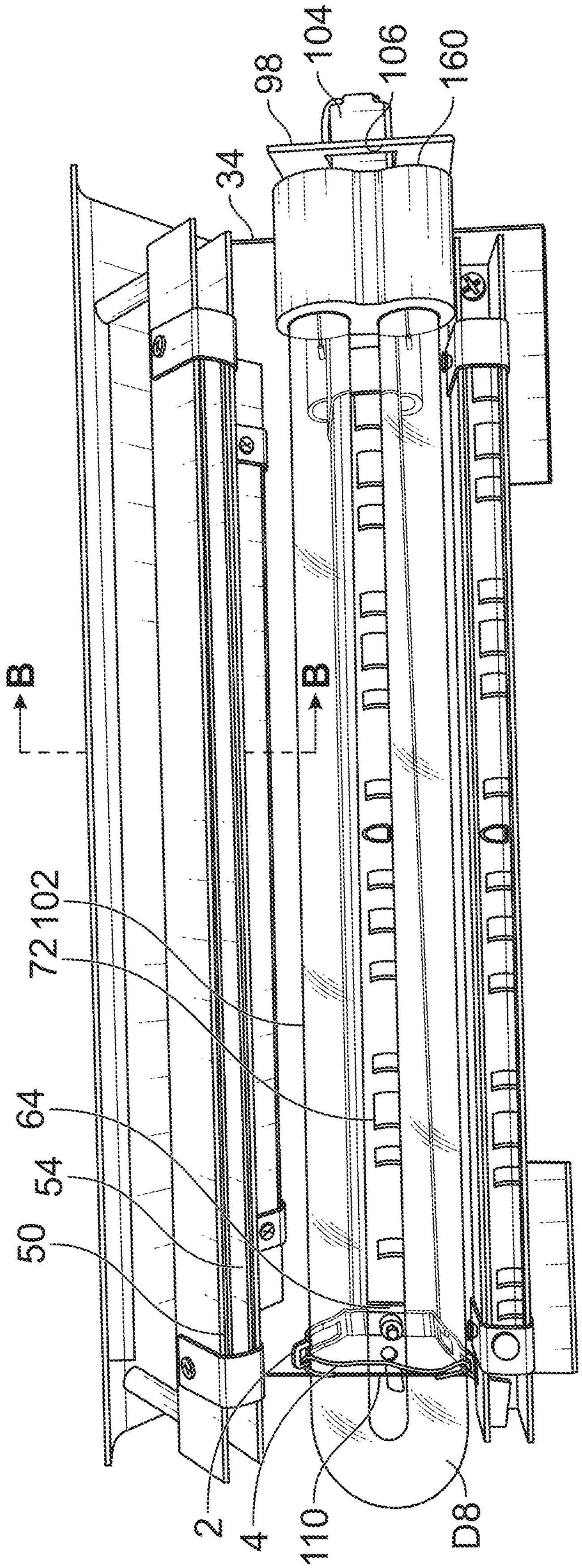
FIG. 12 is an elevation view of the front light assembly.
Figure 13:
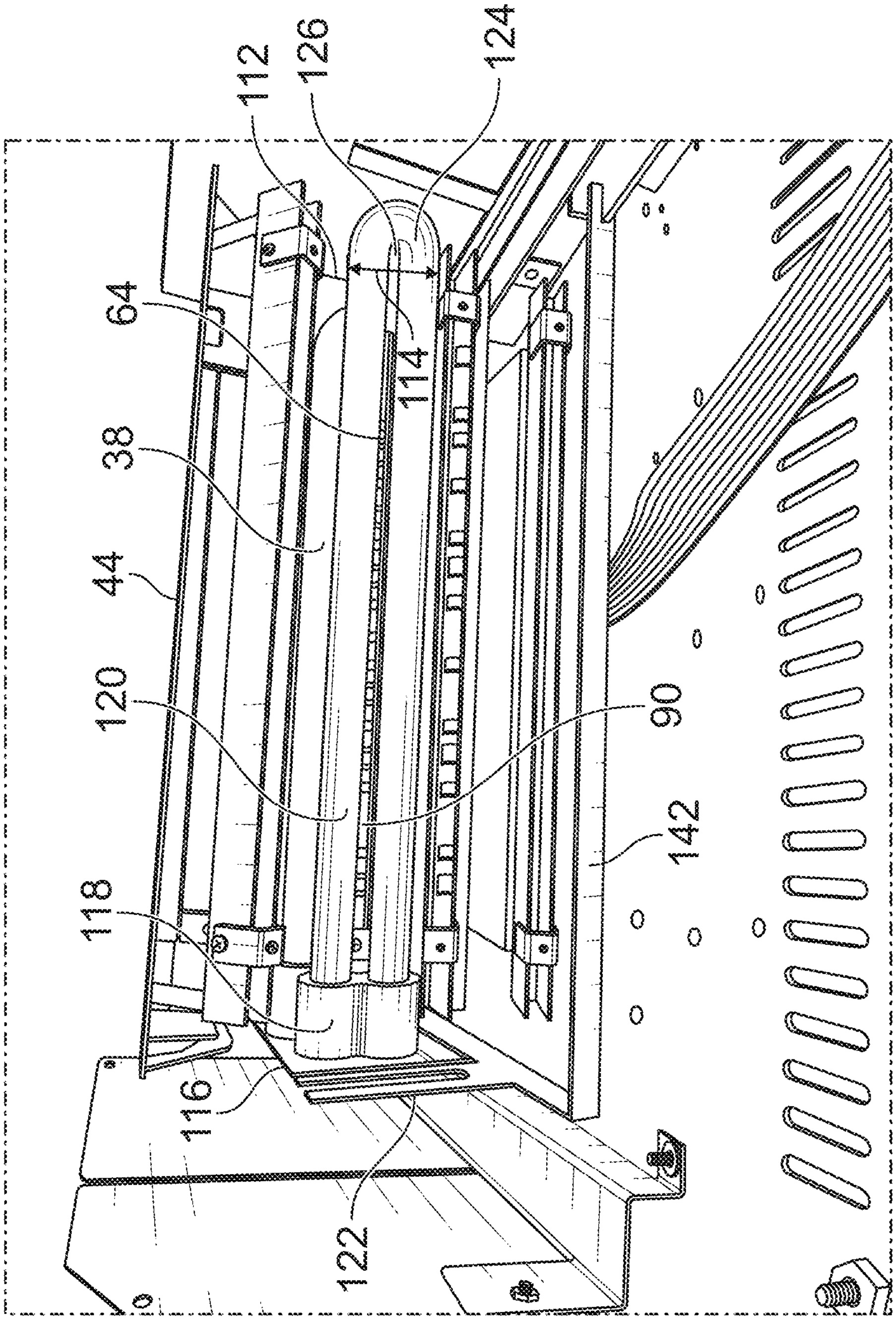
FIG. 13 is a front elevation view of the rear light assembly.
Figure 13A:
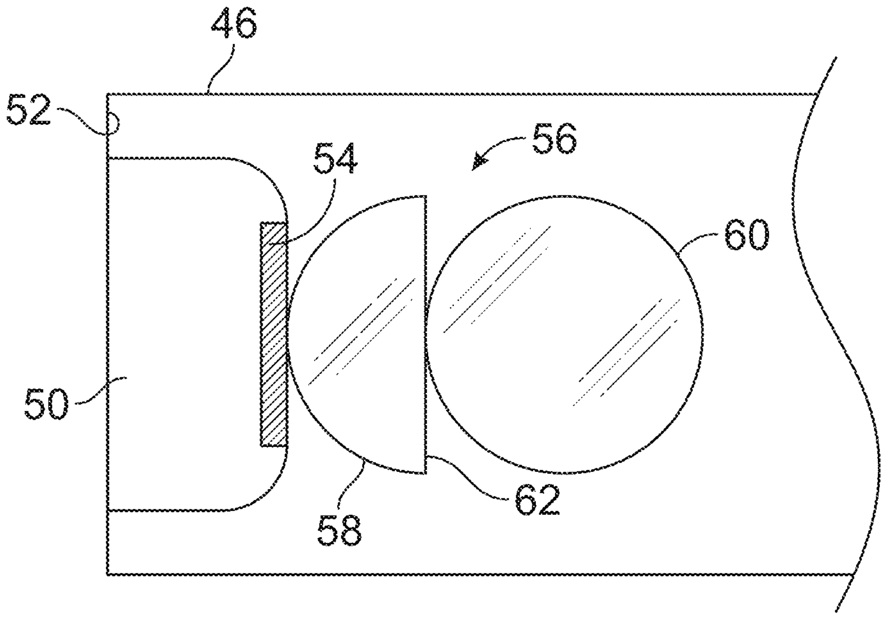
FIG. 13A is a detail cross-section view of each of the LED light assemblies of FIGS. 12 and 13.

Referring to FIG. 13A, which is a cross section view of first LED light housing 46 and green LED light assembly strip 50 taken along line B-B of FIG. 12, light assembly strip 50 is mounted to the base 52 of housing 46. A plurality of green LED lights 54 are attached in a linear array to, or embedded in, strip 50 (FIG. 12) in the channel 56 formed by light housing 46. A half-round clear glass rod or lens 58 is mounted by adhesive or the like over the LED lights 54. A full round clear glass rod or lens 60 is mounted by adhesive or the like to the flat surface 62 of half round glass rod 58. Clips 64 (FIG. 12, 13B) at both ends hold the green LED light assembly strip 50 together.

The green LED light assembly 50 with lenses 58 and 60 described above produces a tight horizontal line of intense visible light highly focused at the line where the upper tube 65 of triple quartz tube cuvette assembly 66 (FIGS. 10, 11) will be located, as explained in detail below. The green LED light assembly 50 focuses and delivers the highest possible concentration of visible light through one upper tube 65 of the quartz tubes comprising cuvette assembly 66 and into the blood as the blood flows through upper tube 65 of cuvette assembly 66. As will be explained, the same concentration of highly focused light is emitted from each of the other LED light assembly strips directed at the several tubes of triple quartz tube cuvette assembly 66.

A second U-shaped LED light housing 70 is attached to reflective surface 36 of front light support panel 34. A double wavelength red LED light assembly strip 72 extends linearly substantially along the horizontal length of second LED light housing 70. As seen in FIGS. 10 and 11, light emanating from red LED light assembly strip 72 will be directed in a concentrated and highly focused linear beam to second or middle tube 74 of cuvette assembly 66. Red LED light assembly strip 72 comprises alternating diodes of different wavelengths along the strip. For example, positions 1, 3, 5, 7, 9 are either 620 nm or 670 nm optimally, and positions 2, 4, 6, 8, 10 are the other of these wavelengths. These wavelengths could also be in the range of 610 nm-685 nm.

Red LED light assembly strip 72 is structurally the same as described above regarding green LED light assembly strip 50, only the LED lights are red rather than green. The description above regarding the lens structure of FIG. 13A is equally applicable to red LED light assembly strip 72, except that the LED lights are red, and the light is directed at middle tube 74 of cuvette assembly 66. The above description of a tight line of intense visible light focused on the upper tube 65 of cuvette assembly 66 applies equally here regarding the red LED light focused on middle tube 74 of cuvette assembly 66.

Referring back to FIGS. 10 and 11, a third U-shaped LED light housing 76 is attached by supports 78 to reflective surface 36 of front light support panel 34. An amber LED light assembly strip 80 extends linearly substantially along the horizontal length of third led light housing 76. As seen in FIGS. 10 and 11, light emanating from amber LED light assembly strip 80 will be directed in a concentrated and highly focused linear beam to third or bottom tube 82 of cuvette assembly 66. Light emanating from amber LED light assembly strip 80 optimally has a wavelength of 590 nm, and could be in the range of 575 nm and 605 nm.

Amber LED light assembly strip 80 is structurally the same as described above regarding green LED light assembly strip 50, only the LED lights are amber rather than green. The description above regarding the lens structure of FIG. 13A is equally applicable to amber LED light assembly strip 80, except that the LED lights are amber, and the light is directed at bottom tube 82 of cuvette assembly 66. The above description of a tight line of intense visible light focused on the upper tube 65 of cuvette assembly 66 applies equally here regarding the amber LED light focused on bottom tube 82 of cuvette assembly 66.

Referring to FIGS. 10 and 11, several LED light sources are mounted on reflective surface 40 of rear light assembly 30. A fourth U-shaped LED light housing 84 is attached by supports 85 to reflective surface 40. Mounted in the channel formed by the U-shape of housing 84 is a blue LED light assembly strip 86 extending substantially the horizontal length of fourth LED light housing 84. Due to the angle of angled portion 44 of rear light support panel 38, light emitted by the blue LED lights in assembly strip 86 is directed downward at an angle towards upper tube 65 of cuvette assembly 66. Light eimanating from blue LED light assembly strip 86 optimally has a wavelength of 450 nm, and could be in the range of 435 to 465 nm.

Blue LED light assembly strip 86 is structurally the same as described above regarding green LED light assembly strip 50, only the LED lights are blue rather than green. The description above regarding the lens structure of FIG. 13A is equally applicable to blue LED light assembly strip 86, except for the color of the LED lights. The above description of a tight line of intense visible light focused on the upper tube 65 of cuvette assembly 66 applies equally here regarding light emanating from blue LED light assembly strip 86.

A fifth U-shaped LED housing 88 is attached directly to reflective surface 40 of rear light support panel 38. Mounted in the channel formed by U-shaped LED housing 88 is an amber LED light assembly strip 90 extending substantially the horizontal length of fifth LED light housing 88. Light emitted by amber LED light assembly strip 90 is directed horizontally directly towards middle tube 74 of cuvette assembly 66 as a highly focused linear light beam. The wavelengths of light from amber LED light assembly strip 90 are the same as described above regarding amber LED light strip 80.

Amber LED light assembly strip 90 is structurally the same as described above regarding green LED light assembly strip 50, only the LED lights are amber rather than green. The description above regarding the lens structure of FIG. 13A is equally applicable to amber LED light assembly strip 90, except for the color of the LED lights. The above description of a tight line of intense visible light focused on the upper tube 65 of cuvette assembly 66 applies equally here regarding light emanating from amber LED light assembly strip 90 and focused on middle tube 74 of cuvette assembly 66.

A sixth U-shaped LED housing 92 is attached by a plurality of supports 94 to reflective surface 40. Mounted in the channel formed by the U-shape of housing 92 is a dual wavelength red LED light assembly strip 96 extending substantially the horizontal length of sixth LED light housing 92. Light emitted by the red LED lights in assembly strip 96 is directed towards bottom tube 82 of cuvette assembly 66. Red LED light assembly strip 96 is structurally the same as described above regarding green LED light assembly strip 50, only the LED lights are red. The description above regarding the lens structure of FIG. 13A is equally applicable to red LED light assembly strip 96, except for the color of the LED lights. The above description of a tight line of intense visible light focused on the upper tube 65 of cuvette assembly 66 applies equally here regarding light emanating from amber red LED light assembly strip 96 and focused on bottom tube 82 of cuvette assembly 66. Red LED light assembly strip 96 comprises alternating diodes of different wavelengths along the strip. For example, positions 1, 3, 5, 7, 9 are either 620 nm or 670 nm, and positions 2, 4, 6, 8, 10 are the other of the wavelengths.

Referring to FIG. 12, a rigid bracket 98 extends laterally from front light support panel 34. The base 100 of a high output UVC light source 102 in the range of 253.7 nm is firmly mounted to bracket 98, with a power connector 104 extending through aperture 106 in bracket 98. UVC light source 102 comprises a U-shaped fluorescent tube 108 as is known in the art. A space 110 is formed between each pass of U-shaped tube 108 for purposes to be described.

Figure 13B:
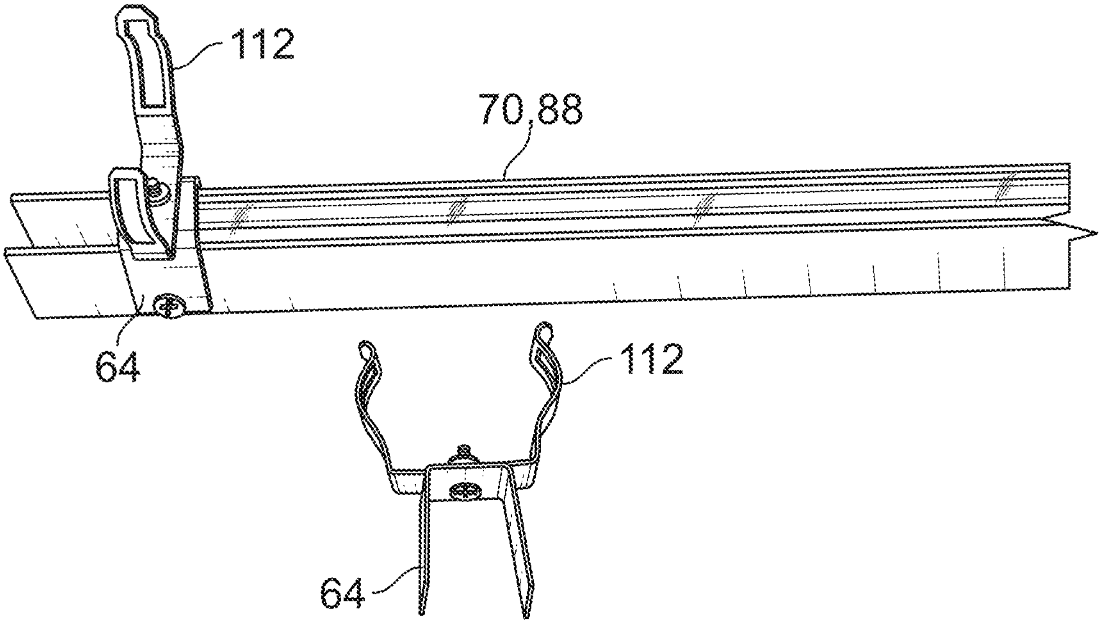
FIG. 13B is a detail view of a bracket used to secure the U-shaped end of the UVA and UVC light tubes to their respective light assemblies.

Referring to FIG. 13B and FIG. 12, clip 64 supporting red LED light assembly strip 72 in second LED light housing 70 includes a U-shaped bracket 112 that extends adjacent the outer surface of UVC tube 108, securing tube 108 vertically. Wire 114 extends between the open ends of bracket 112 to secure U-shaped tube 108 horizontally. As seen in FIGS. 11 and 12, focused light emanating from red LED light assembly strip 72 will travel in space 110 unimpeded before being focused on middle tube 74 of cuvette assembly 66. In similar fashion, amber LED light assembly strip 80 is located below U-shaped UVC tube 108, allowing focused light to pass from amber LED light assembly strip 80 to bottom tube 82 of cuvette assembly 66.

Referring to FIG. 13, a rigid bracket 116 extends laterally from rear light support panel 38. The base 118 of a high power dual wavelength UVA light source 120 emitting UVA light in wavelengths of 340 nm and 365 nm is firmly mounted to bracket 116, with a power connector 122 extending through an aperture (not shown) in bracket 116. UVA light source 120 comprises a U-shaped fluorescent tube 124 as is known in the art. A space 126 is formed between each pass of U-shaped UVA tube 124 for purposes to be described.

Referring to FIG. 13B and FIG. 13, clip 64 holding amber LED light assembly strip 90 in fifth LED light housing 88 includes a second U-shaped bracket 112 that extends adjacent the outer surfaces of UVA tube 120, securing tube 120 vertically. Second wire 114 extends between the open ends of second bracket 112 to secure U-shaped tube 124 horizontally. As seen in FIGS. 11 and 13, focused light emanating from amber LED light assembly strip 90 will travel in space 126 unimpeded before being focused on middle tube 74 of cuvette assembly 66. In similar fashion, red LED light assembly strip 96 is located below U-shaped UVA tube 120, allowing focused light to pass from red LED light assembly strip 96 to bottom tube 82 of cuvette assembly 66.

Figure 14:
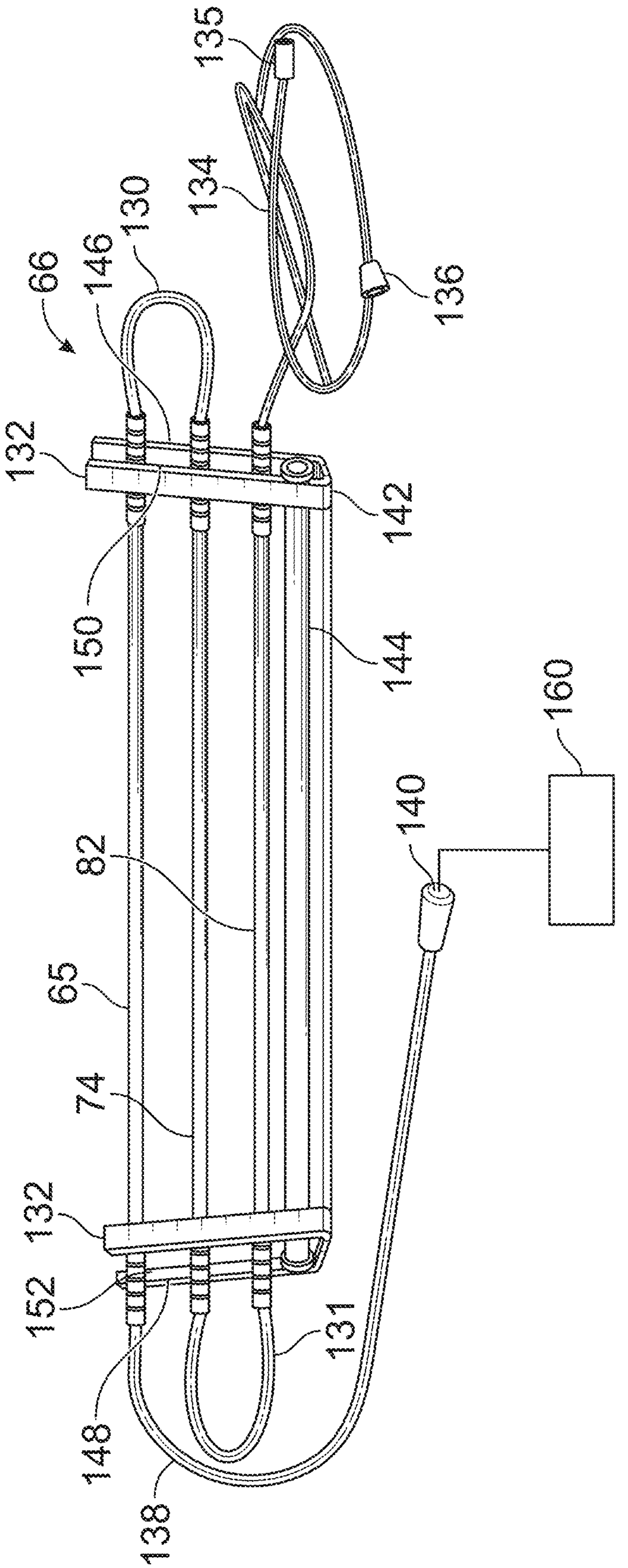
FIG. 14 is a front perspective detail view of the triple quartz tube cuvette assembly of the first embodiment of the polychromatic phototherapy device.

Referring to FIG. 14, the disposable triple quartz tube cuvette assembly 66 of the presently disclosed device is shown. Cuvette assembly 66 comprises three hollow quartz tubes 65, 74, 82 mounted parallel to each other. Flexible loop 130 connects tube 65 to tube 74 and flexible tube 131 connects tube 74 to tube 82, providing a single path for blood to flow in either direction through cuvette assembly 66. A pair of cuvette supports 132 hold opposite ends of tubes 65, 74 and 82 in their proper vertical location, as will be explained. Inlet tubing lead 134 is attached to tube 82 and is adapted to communicate at end 135 with a standard infusion set for withdrawing blood from a patient. A port 136 is adapted to connect inlet tubing lead 134 with a syringe if needed to treat clogging or any other anomalies in the blood stream. Inlet tubing lead 134 is connected to bottom tube 82 of cuvette tube 128 on the patient side. Outlet tubing lead 138 is connected to upper tube 65 of cuvette assembly 66, and to a reservoir 160 at end 140 of outlet tubing lead 138.

Figure 15:
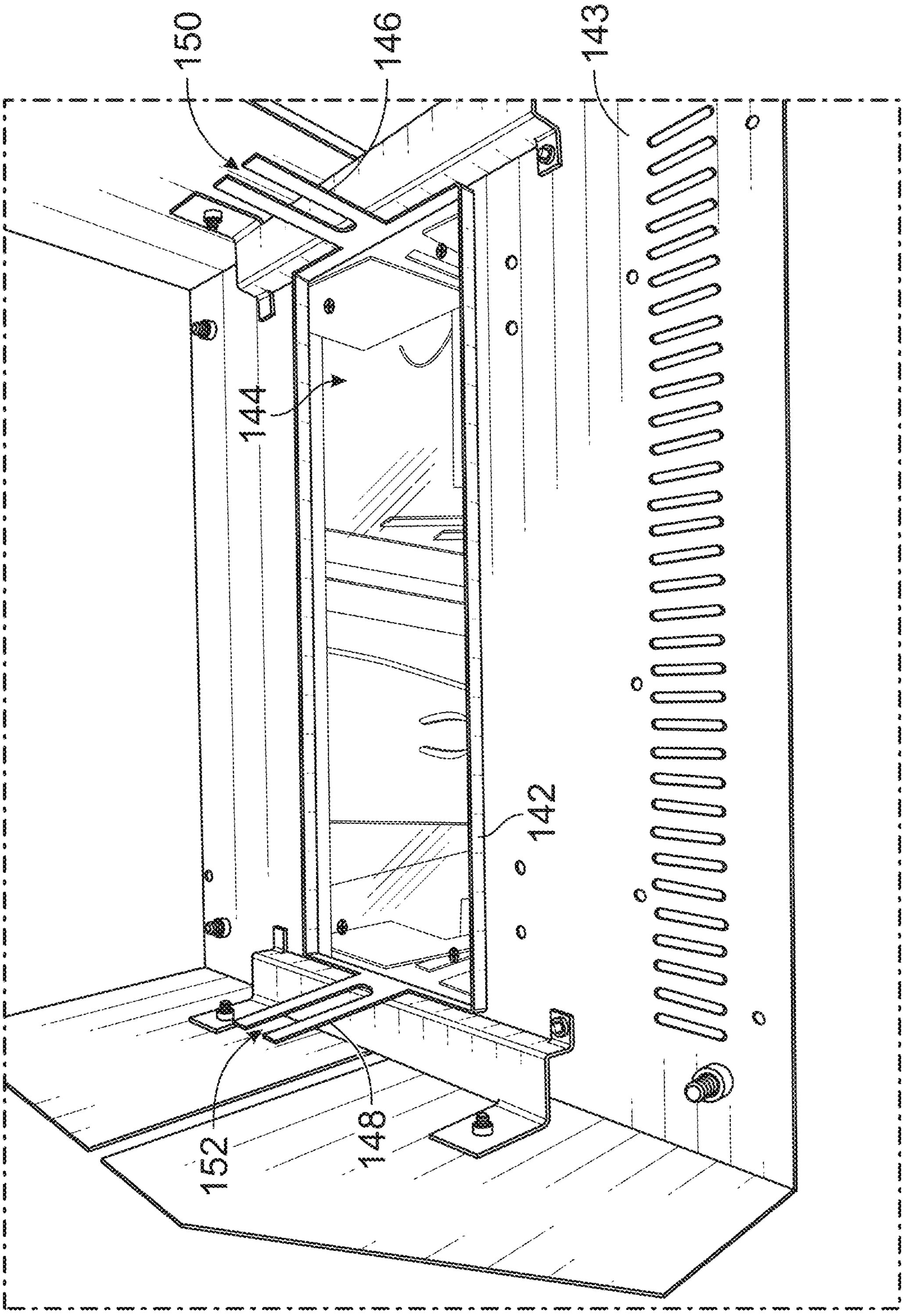
FIG. 15 is a detail perspective view of the reflective tray that removably supports the triple quartz tube cuvette assembly of FIG. 14.

Also illustrated in FIGS. 14 and 15 is reflective tray 142 attached to the bottom surface 143 (FIG. 15) of housing 11. Tray 142 has a reflective top surface 144 that assists in reflecting light from the various UV and LED light sources to tubes 65, 74 and 82 of cuvette assembly 66. Opposed brackets 146, 148 extend upward from reflective tray 142, and slots 150, 152 are adapted to receive the portions of tubes 65, 74 and 82 extending outwardly beyond cuvette supports 132. Open top slots 150, 152 support cuvette assembly 66 in a correct vertical position when cuvette assembly 66 is placed in treatment chamber 32 between the front and rear light sources. When tube 128 is properly located in slots 150, 152, disposable cuvette assembly 66 can be manually inserted in and removed from treatment chamber 32 in housing 11. When cuvette assembly 66 is fully inserted into slots 150, 152, the bottom of each cuvette support 132 rests on reflective surface 144 of tray 142 to properly vertically position tubes 65, 74 and 82, in relation to the various light sources described above.

Figure 7:
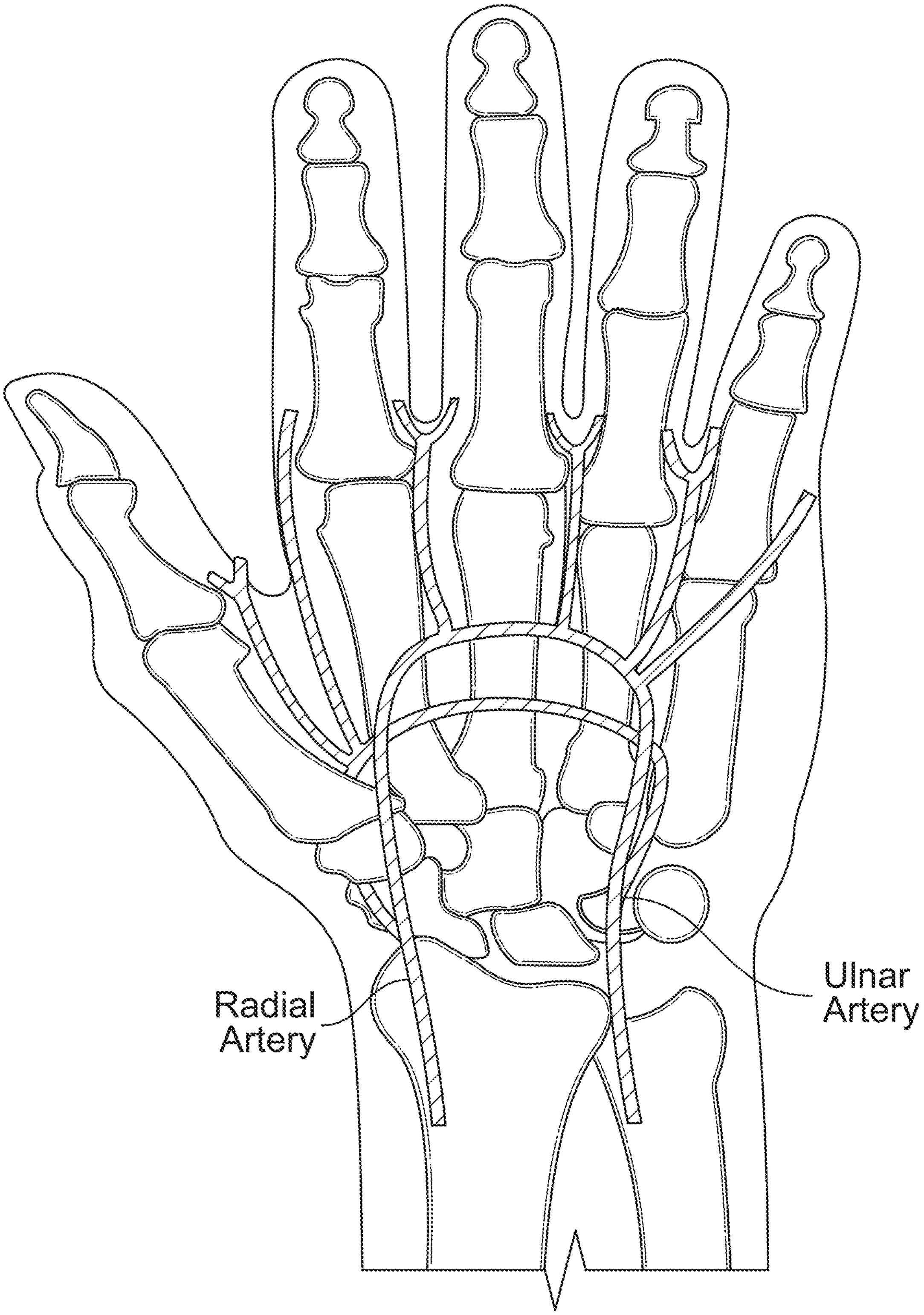
FIG. 7 is a diagram showing the radial artery and the ulnar artery of a human hand.
Figure 16:
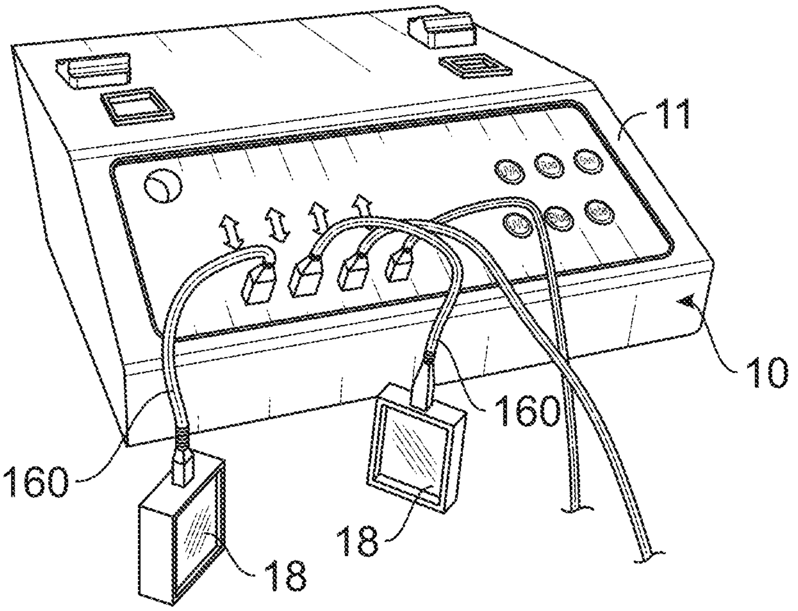
FIG. 16 is a front perspective view of the first embodiment of the polychromatic phototherapy device, showing a pair of wrist pads in accordance with implementations of this disclosure.

FIGS. 16 and 17 illustrate a topical wrist pad 18 comprising a densely populated plurality of deep red/photored LED lights 156 on surface 154 to promote a photodynamic therapy treatment and increase blood circulation when wrist pad 18 is applied to a patient's wrist using strap 156. FIG. 16 illustrates two wrist pads. Each wrist pad 18 is powered by electrically connecting the wrist pad to a USB port 16 (FIG. 9) via a power cord 160 (FIG. 16). When activated, the wavelengths of the red LED lights 156 stimulate an immune system response in the patient. This is significant for blood flow, is deeply penetrating, and is easy to access via the radial and ulnar arteries (FIG. 7). The intensity of the deep red/photored LED lights 156 is controlled by the intensity dome switch 14 above the USB port 16 into which wire or wires 160 are inserted (FIG. 16).

Referring to FIG. 17, the wavelengths of red LED lights L1, L3, L5, L7 and L9 are all one of either approximately 625 nm or approximately 650 nm. The wavelengths of red LED lights L2, L4, L6, L8 and L10 would be the other of those two wavelengths.

The high power dual wavelength UVA light source 120 (FIG. 13) includes a custom made U-shaped high output bulb 124 that emits the primary wavelength that stimulates NADH and NAD+ in blood. The high output UVC light source 102 (FIG. 13) includes a high output bulb 108 in the primary germicidal UVC band, which stimulates NAD and general germicidal and virus inactivation in blood. The device 10 in the illustrated embodiment utilizes very specialized custom made bulbs, constructing photonic architecture that supports and up regulates NAD+ and NADH, which are integral for the resultant production of ATP. The device 10 can also provide up regulation of the chylomicron albumen component of the blood.

Red LED lights in assemblies 72 and 96 (FIG. 10), which in this exemplary implementation emit light in wavelengths of approximately 620 nm and 670 nm, support the outer valence of the primary enzymes, such as super oxide dismutase (S.O.D.), catalese, and the other elements of our primary nucleotides, and promote and increase mitochondrial energy. Red light wavelengths stimulate immune response.

Amber LED light assemblies 80, 90, which in this exemplary implementation emit light in wavelengths of approximately 590 nm, support production and release of NO. Recent findings indicate that low intensity light (590 nm±14 nm) stimulates Cco/NO activity under both hypoxic and, to a lesser extent, normoxic conditions, providing an alternative explanation for the increase in NO bioavailability observed during photomodulation. These new findings indicate that low level light stimulates new NO synthesis from Cco/NO and does not merely release NO from pre-existing tissue stores. Because the NO produced by Cco/NO can be used both inside cells, where it functions in hypoxic signaling, and outside of cells, where it may function in vasodilation and other signaling pathways, it is likely to have a multitude of effects. Additionally, the use of the amber source in combination with St. John's Wort helps promote wellbeing and reversing depression, which is very important in the treatment of cancers and chronic conditions. The use of St. John's Wort and, if desired, curcumin for three days prior to treatment with the device 10 is recommended to enhance anti-depression results. The resulting elevated serotonin level helps all treatment therapies to be better tolerated as it improves mood.

It has been established that low level laser therapy, when used on human blood in vitro, affects the rheology of erythrocytes and leucocytes. It has also been observed that low level laser therapy changes the erytherocytatory, leucocytatory, BSR, and aggregability indices of blood. Therefore, green LED light assembly 50, which in this exemplary implementation emits light in a wavelength of approximately 525 nm, can affect the physical as well as chemical properties of blood cells, which is not only helpful in the preservation of blood but also in revitalizing the physically and chemically stressed erytherocytatory membranes. It has been determined that the light decreases the viscosity of blood, thus increasing the electrophoretic mobility of erythrocytes. The green LED light affects the rheology of erythrocytes and leucocytes, and chemical properties of blood cells revitalizing the physically and chemically stressed erythrocytatory membranes. Blue-green light is also known to balance the redox processes within the cells.

Blue LED light assembly 86, which in this exemplary implementation emits light in a wavelength of approximately 450 nm, promotes vasodilation while reducing inflammation, improving blood flow, and delivering increased oxygen and nutrients to cells. Blue light also promotes circulation as well as having additional anti-bacterial properties. Additionally, blue light has anti-pathogenic properties.

The cuvette assembly 66 (FIG. 14) comprises three connected hollow quartz tubes each tube comprising an approximate twelve inch portion in a parallel arrangement. The sterile, disposable cuvette assembly 66 has 300% of the surface area as any other cuvette assembly available today, which lengthens the time blood components are exposed to the photonic energy by 300% and facilitates three times the energy absorption and triple the exposure "travel" time. The treatment chamber 32 (FIG. 10) is accessed by lifting up access panel 20 of the device 10 using dual pressure latches 26 (FIG. 9), to open and access the treatment chamber 32 for insertion and removal of the cuvette assembly 66. The cuvette assembly 66 is mounted on the brackets 146, 148 located in the treatment chamber 32. Only the cuvette assembly, and the blood that travels through it, will be exposed to the LED light. The cuvette assembly 66 is inserted into the treatment chamber 32 with the flexible tube 138 exiting the device 10 through the slots 150, 152 provided in brackets 146, 148, with the input tubing lead 135 at the bottom of the cuvette assembly 66 on the patient side (FIG. 14). This way the blood flow will start at the bottom of the cuvette assembly 66. As the blood enters the triple tube quartz cuvette assembly 66, the blood's initial exposure is to a short band red wavelength 96 which significantly upgrades the primary protective enzymes, such as S.O.D. and catalase that maintain the red blood cells' ability to be exposed to the additional light wavelengths of the device 10 with no danger of generating met heme.

Blood is drawn directly from the patient through the cuvette assembly 66 and connected tubing into a reservoir 160, (FIG. 14). Photoluminescence exposure occurs in both directions, when the blood is drawn from, and returned to, the patient. The polychromatic phototherapy device 10 enables the medical professional to increase contact time and/or exposure of the blood 300%-600% longer than existing devices. The device's 10 power and light sources are controlled by on-off switches 12 and/or adjustment control dome switches 14 on the face of the device 10 (FIG. 9).

The device 10 cooling mechanism includes a plurality of high flow cooling fans suitably placed in housing 11 to maintain proper operating temperature and to keep internal electronics within optimal operating temperatures. An adequate number of cooling fans are disposed on the inside surface of a rear panel (not shown) of the device 10. An additional assembly of cooling fans are disposed on the inside surface of the front panel of the device 10. The fan arrangement is optimally designed to pull air into the treatment chamber 32 through apertures in the front of the device through louvers in the bottom of housing 11. Air is extracted from housing 11 by means of a plurality of high CFM (cubic feet per minute) fans in the rear panel to provide cooling of the high intensity light sources and to extract heated air. The U-shaped bulb UV lamps 108, 124 are housed in the device 10 in such a manner as to stabilize and maintain proper operating temperature and eliminate any foreign matter contact. A thermal infused type ETL, CSA, and CE line filter (not shown) is employed to significantly reduce system electromagnetic emissions. A high output power supply is provided, as is known in the art.

Several items are required for treatment with the illustrated embodiment of the polychromatic phototherapy device 10, including, but not limited to, one 10 cc syringe, alcohol preps, cotton balls, or wipes, bandage, two clamps, 50 cc of normal saline or greater, one vented UV tubing set (only used with vacuum bottle or bag), one sterile cuvette cartridge 66, one cc of 5,000 units + or − of heparin or equivalent sodium citrate for blood thinning to prevent clotting during treatment, one tourniquet, one 250 cc or 500 cc sterile evacuated container for vacutainer procedure, 60 cc syringes, 2×2 gauze pads, typical 19-21 gauge butterfly needle or 20-22 gauge angio-catheter, and disposable gloves.

The photoluminescence treatment procedure can be administered using the device 10 in several ways. In this implementation, the device 10 can be used to administer the photoluminescence treatment using the push-pull syringe technique, the saline bag infusion technique, the in-line multipass Zotsmann or Hermann hyperbaric ozone technique, and the veterinary syringe technique.

As a general rule of thumb, patients must be well hydrated prior to treatment to promote case of blood flow. The patient may be further hydrated intravenously prior to treatment. Additionally, the operator must ensure that the patient ate prior to treatment and that the patient's blood sugar is in normal range. Before beginning treatment with any of these procedures, the operator must weigh the patient and calculate the amount of blood to withdraw using the following formula:

Weight (in pounds)×1.5=number of cc's of blood to draw.

If the amount of blood to be treated is less than 250 cc, a mark is placed on the bottle where the appropriate amount of blood will have been withdrawn. The area where the procedure is conducted should be hygienically clean and the operator should have all needed supplies at hand. A reclining chair should be provided to allow the patient to recline in the event of lightheadedness, or similar symptoms, while the procedure is progressing.

It is also recommended that the patient take St. John's Wort or curcumin for three days prior to treatment as these molecules promote the release of nitric oxide and also affect a general state of wellbeing as a resultant reaction to the absorption of wavelengths emitted by the polychromatic phototherapy device 10.

Certain techniques described below are easier to perform if gravity is used to promote aspiration and reinfusion. Therefore, for aspiration the device 10 should be positioned below the veinipuncture and the reservoir blood collection bag or bottle 160 below that point. Reversing the positions would aid in reinfusion.

Figure 18:
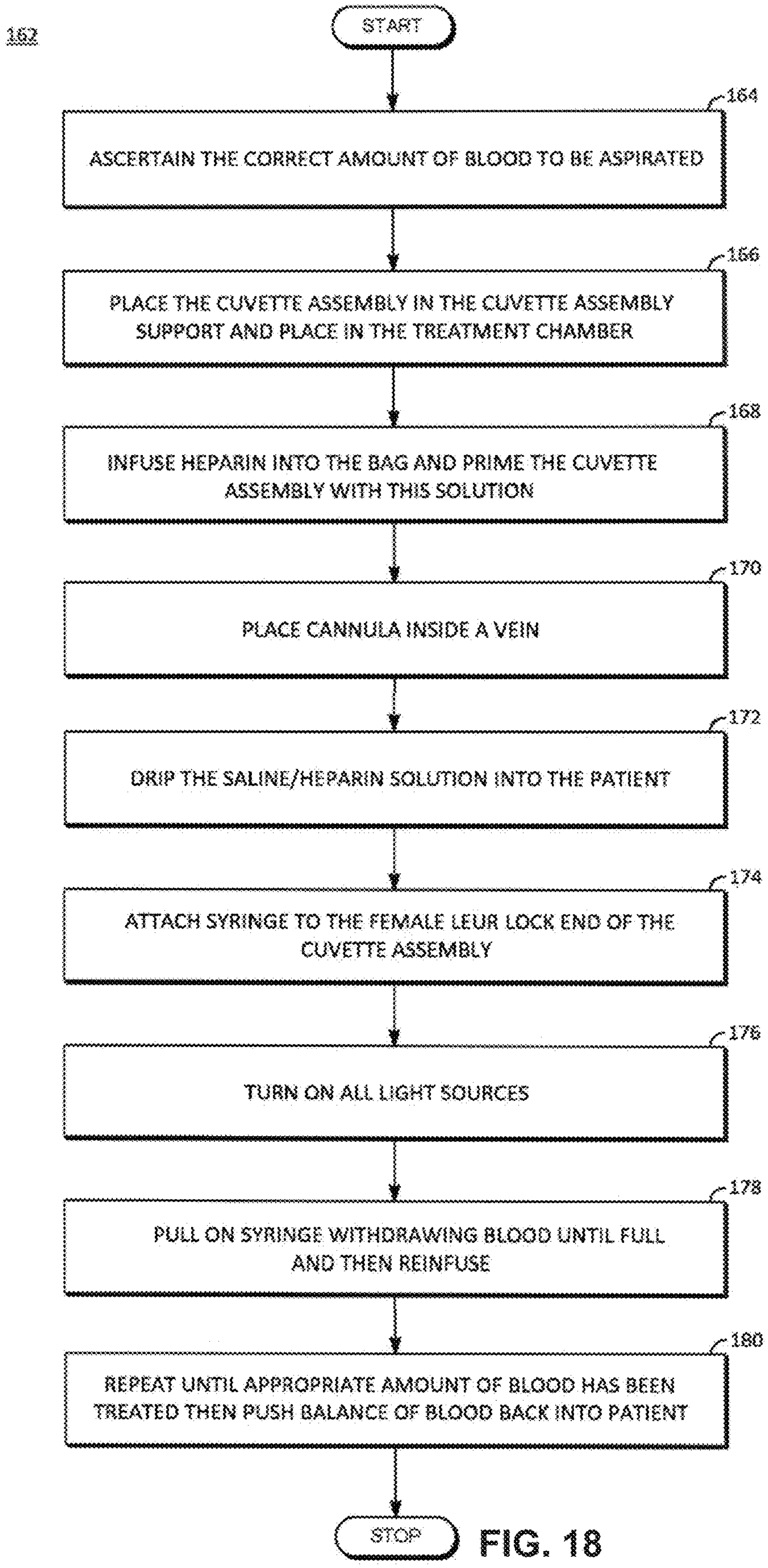
FIG. 18 is a flow diagram of a process for treating blood with the polychromatic phototherapy device using a push-pull syringe technique in accordance with implementations of this disclosure.

FIG. 18 is a flow diagram showing a process 162 for treating blood using the polychromatic phototherapy device 10 in accordance with an implementation of this disclosure. Process 162 uses a push-pull syringe technique that begins by ascertaining the correct amount of blood to be aspirated 164 by the pre-approved doctor's protocol using the Knott Technique, 1 to 1.5 cc to 1 pound of body weight as indicated above and selecting an appropriate size bag of normal saline, either 250 cc or 500 cc, and hanging the bag on an IV pole. The cuvette assembly 66 is then placed in the treatment chamber 32 in the device 10, 166, taking care to be certain that the cuvette assembly 66 is resting on the reflective tray 142 (FIG. 10) of the treatment chamber 32.

Infuse the appropriate amount of heparin into the bag, for example 2500-4000 units, and prime the cuvette cartridge 66 with this solution 168. Prepare the venous site by cleansing the area with an alcohol prep. Place a cuff on the patient's arm and inflate to between 90-100 mm Hg, or use a tourniquet.

Once an appropriate site has been located, proceed with cannulation using either a 19-21 gauge butterfly or a 20-22 gauge catheter 170. As light has significant biological benefits, you may turn on all visible light sources, LEDs red, amber, green, and blue, during this infusion process. Drip the majority of the saline/heparin solution into the patient 172. For example, if using a 250 cc saline bag the operator may want to infuse 150 cc of the saline, or in the case of a 500 cc saline bag the operator may want to infuse 350 cc of saline, into the patient. Now the patient has been heparinized and has received some hydration. Attach a 60 cc syringe to the female Leur lock end of the cuvette cartridge 66, 174. Optionally, place topical wrist pads 18 (FIGS. 16, 17) on the patient to administer photodynamic therapy treatment, in this illustrated embodiment, using liposomal methylene blue.

There are adjustments for intensity on the device 10. Adjust intensity using the intensity dome switches 14 above the USB port 16 for each device. Full intensity is recommended unless this is too uncomfortable for the patient. Turn on all light sources by using switches 12. Release tourniquet or cuff pressure and gently pull on syringe plunger withdrawing blood until full, then reinfuse 178. It is sometimes advisable to flush the veinipuncture area with heplock to prevent clotting before starting the flow of blood from the patient and when returning blood to the patient. The cuvette assembly 66 has an additional lead with port 134 to make this more convenient. If the pressure is too great in either direction, do not push harder as a rupture in the cuvette cartridge 66 may occur. Stop and turn off all light sources. Determine the cause of the clotting, which is usually at the veinipuncture. Clear the clot, reactivate all light sources and continue. Repeat until the appropriate quantity of blood has been treated and then attach a syringe with saline and push the balance of blood back into the patient 180. Once the treatment has been completed, dispose of all materials appropriately.

Figure 8:
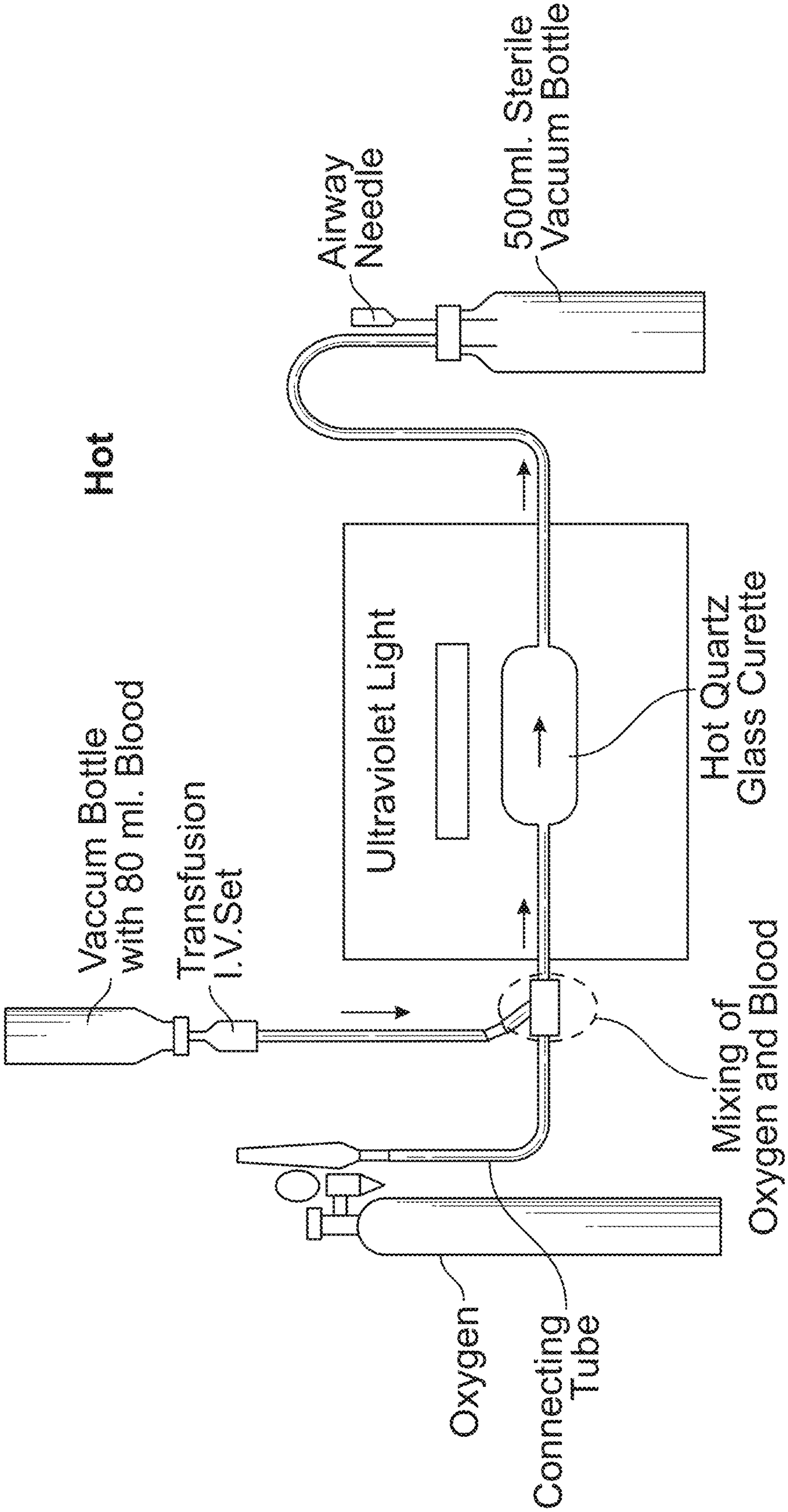
FIG. 8 is a diagram showing ozone therapy.
Figure 19:
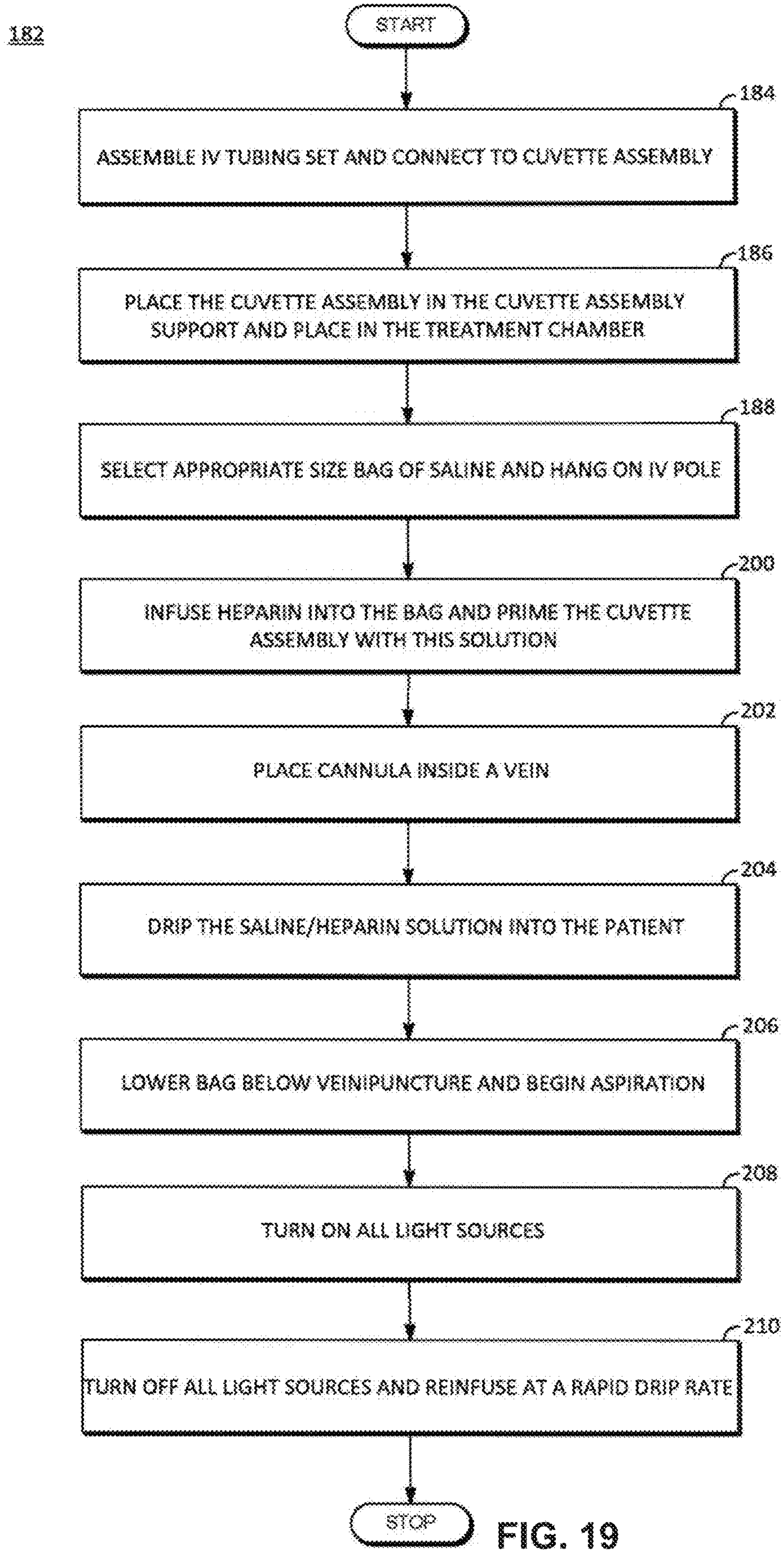
FIG. 19 is a flow diagram of a process for treating blood with the polychromatic phototherapy device using a saline bag infusion technique in accordance with implementations of this disclosure.

FIG. 19 is a flow diagram showing a process 182 for treating blood using the polychromatic phototherapy device 10 in accordance with an implementation of this disclosure. Process 182 uses a saline bag infusion technique that begins by assembling an I.V. (infusion set) tubing set and sterilizing cuvette assembly 66, 184. Do not use a filter of any kind as it may restrict blood flow. Connect tubing set to cuvette assembly 66 using sterile technique creating a closed system. Care must be taken not to touch the surface of the cuvette assembly 66 tubes, as fingerprints will impede penetration of the UV light sources. If fingerprints or body oils are inadvertently left on the quartz tubes of the cuvette assembly 66 surface, wipe off with plain alcohol. The cuvette assembly 66 is placed in the treatment chamber 32 in the device 10, 186, taking care to be certain that the cuvette assembly is resting on the reflective tray 142 of the treatment chamber 32. Handle the cuvette assembly 66 by placing the cuvette assembly 66 into the treatment chamber 32 of the device 10, or by the standoffs or flexible tubing of the cuvette assembly 66. Follow procedures for attaching and adjusting optional topical pads, if used, as described above. Select an appropriate size bag of normal saline, either 250 cc or 500 cc, and hang on an IV pole 188. Infuse the appropriate amount of heparin, for example 2500-5000 units, and prime the cuvette assembly 66 with this solution 200. Establish a veinipuncture using either a 19 gauge butterfly or a 20 gauge catheter 202. Drip the majority of the saline/heparin solution into the patient 204. For example, if using a 250 cc saline bag the operator may want to infuse 150 cc of the saline, or in the case of a 500 cc saline bag the operator may want to infuse 350 cc of saline, into the patient. Now the patient has been heparinized and has received some hydration. Lower the saline/collection bag below the site of the veinipuncture and begin aspiration 206. Turn on all light sources 208. Gravity will assist in the collection of the desired amount of blood. When the desired quantity of blood has been collected, turn off all light sources 210. Raise the bag and reinfuse at a rapid drip rate 210, at least 10 cc per minute. Ozone (FIG. 8) may be added for additional oxidative enhancement if desired. Ozone may be infused into the bag with the collected blood with syringes up to the amount of the blood in the bag, 1 to 1. When all blood has been returned to the patient, dispose of all materials as appropriate.

Figure 20:
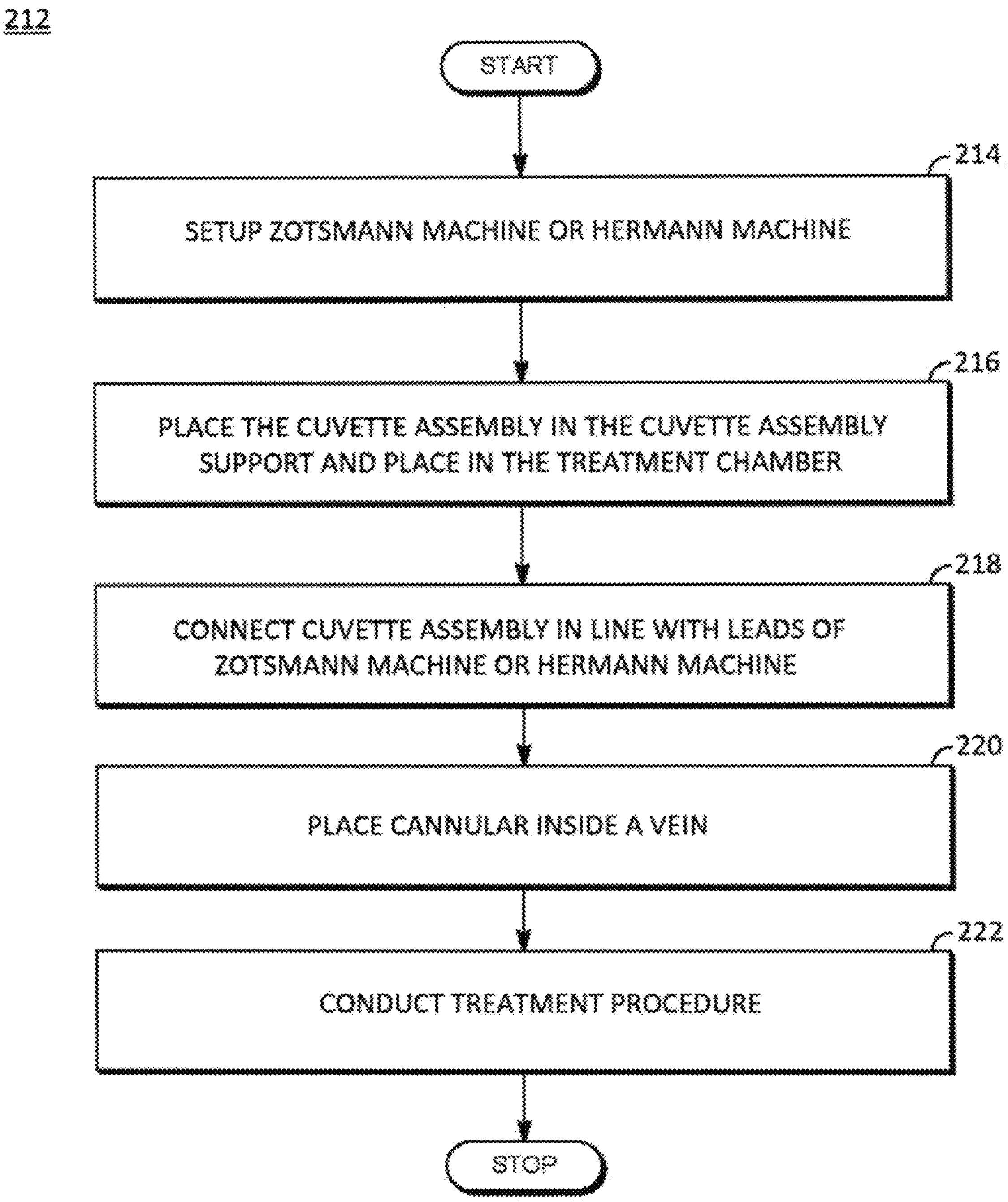
FIG. 20 is a flow diagram of a process for treating blood with the polychromatic phototherapy device using an in-line multipass Zotsmann or Hermann hyperbaric ozone technique in accordance with implementations of this disclosure.

FIG. 20 is a flow diagram showing a process 212 for treating blood using the polychromatic phototherapy device 10 in accordance with an implementation of this disclosure. Process 212 uses an in-line multipass Zotsmann or Hermann hyperbaric ozone technique that begins with following all preparation procedures as indicated previously and setting up the Zotsmann machine (not shown) or the Hermann machine (not shown) 214, following their respective setup procedures as described by their manufacturers. The cuvette assembly 66 is placed in the treatment chamber 32 in the device 10, 216, taking care to be certain that the cuvette assembly 66 is resting on the reflective tray 142 of the treatment chamber 32. Connect the cuvette assembly 66, which has been inserted into the treatment chamber 32 of the device 10, in line with the leads for each of the Zotsmann device or the Hermann device 218. The device 10 is connected in line with either the Zotsmann device or the Hermann device, which pull and push the blood through the cuvette assembly 66 into a container and then reinfuse back through the cuvette assembly 66 into the body from the same cannula as the blood had been withdrawn 220. Conduct the treatment procedure as normal with either of them 222, making sure that pressure does not exceed 0.7 atm (atmospheres) as indicated on either device.

Figure 21:
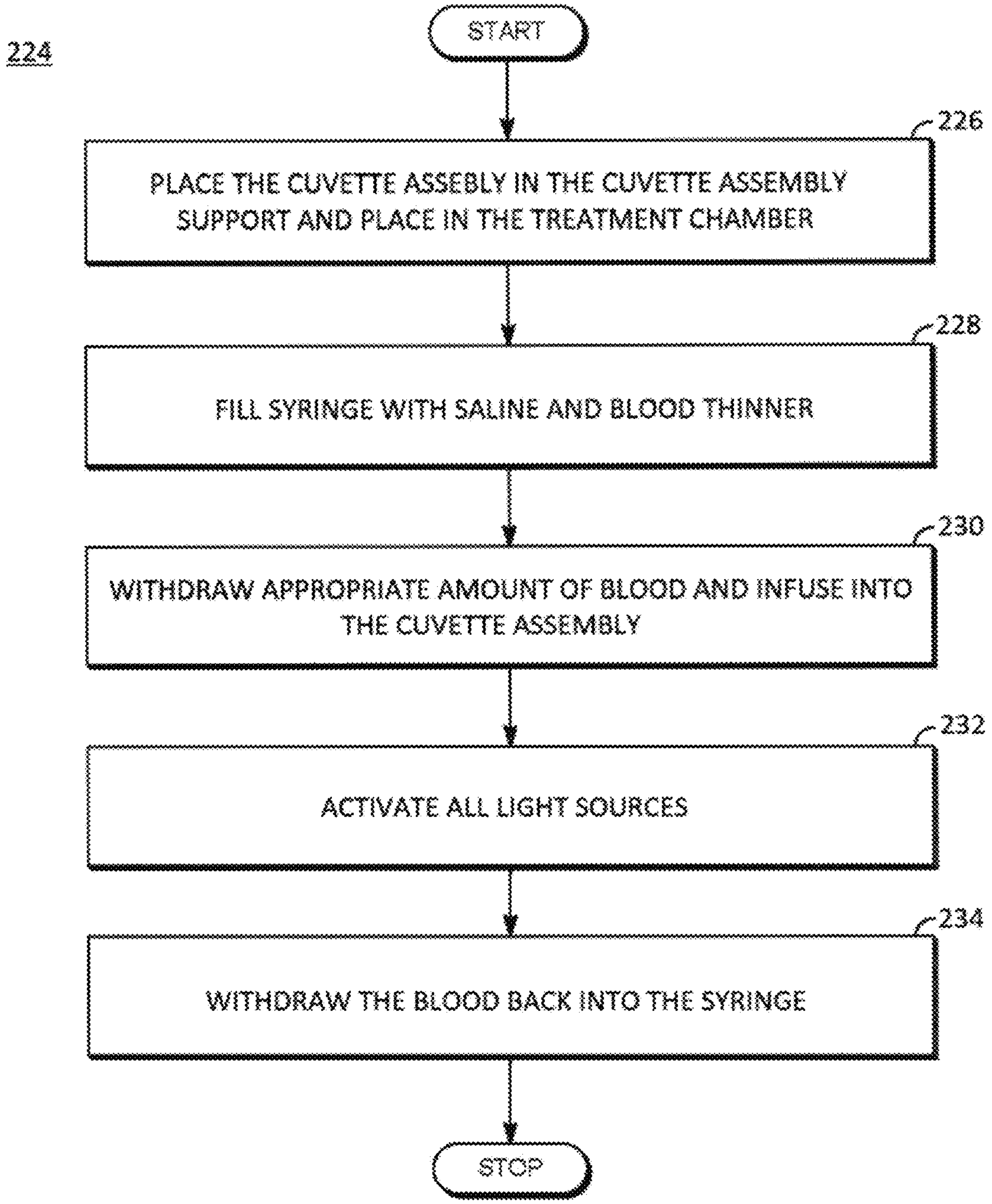
FIG. 21 is a flow diagram of a process for treating blood with the polychromatic phototherapy device using a first embodiment of a veterinary syringe technique in accordance with implementations of this disclosure.

FIG. 21 is a flow diagram showing a process 224 for treating blood using the polychromatic phototherapy device 10 in accordance with an implementation of this disclosure. Process 224 uses a first embodiment of a veterinary syringe technique. As our four legged friends are generally much smaller in body weight than we are, only about 1.5 cc of blood per pound of body weight should be treated. Process 224 uses a sterilized cuvette assembly 66. Do not use a filter of any kind as it may restrict blood flow. Connect the tubing set to cuvette assembly 66 using sterile technique creating a closed system. Care must be taken not to touch the surface of the cuvette assembly 66 quartz tubes, as fingerprints will impede penetration of the UV sources. If fingerprints or body oils are inadvertently left on the quartz tubes of the cuvette assembly 66 surface, wipe off with plain alcohol. The cuvette assembly 66 is placed in the treatment chamber 32 in the device 10, 206, taking care to be certain that the cuvette assembly 66 is resting on reflective tray 142 of the treatment chamber 32. Handle the cuvette assembly 66 by placing the cuvette assembly 66 into the treatment chamber 12 of the device 10, or by the standoffs or flexible tubing of the cuvette assembly 66. The cuvette assembly 66 and associated tubing hold approximately 30 cc of fluids, therefore fill a syringe with some saline and blood thinner, possibly heparin, in an amount determined to be appropriate 228. Withdraw the amount of blood determined to be appropriate and infuse into the cuvette assembly 66, 230. Activate the light sources 232 and wait 30 seconds. Withdraw the blood back into the syringe 234. Repeat the process as required.

Figure 22:
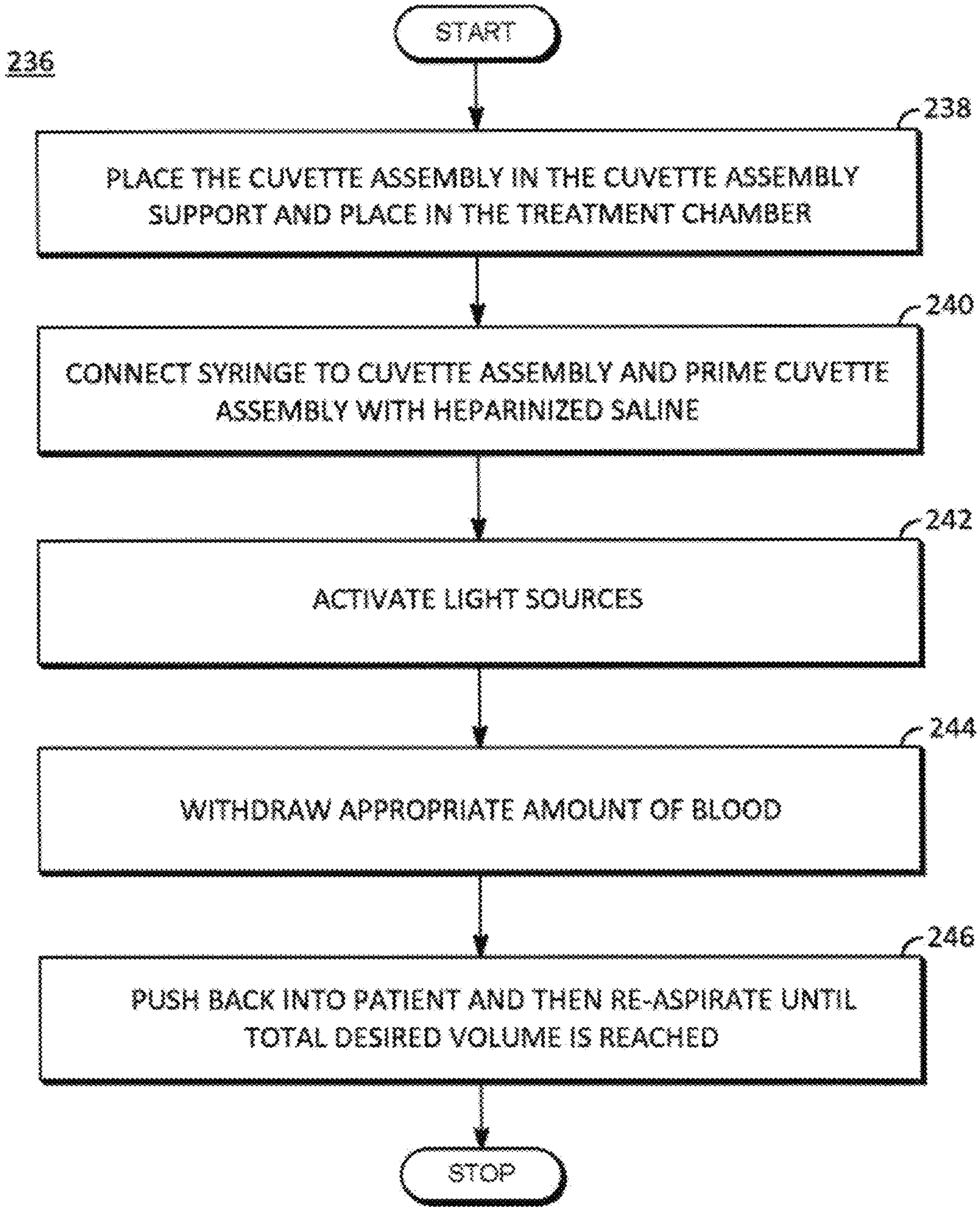
FIG. 22 is a flow diagram of a process for treating blood with the polychromatic phototherapy device using a second embodiment of a veterinary syringe technique in accordance with implementations of this disclosure.

FIG. 22 is a flow diagram showing a process 236 for treating blood using the polychromatic phototherapy device 10 in accordance with an implementation of this disclosure. Process 236 uses a second embodiment of a veterinary syringe technique. Process 236 uses a sterilized cuvette assembly 66. Do not use a filter of any kind as it may restrict blood flow. Connect the tubing set to cuvette assembly 66 using sterile techniques creating a closed system. Care must be taken not to touch the surface of the quartz tubes of the cuvette assembly 66 tubes, as fingerprints will impede penetration of the UV sources. If fingerprints or body oils are inadvertently left on the cuvette assembly 66 surface, wipe off with plain alcohol. The cuvette assembly 66 is placed in the treatment chamber 32 in the device 10, 238, taking care to be certain that cuvette assembly 66 is resting on reflective tray 142 of the treatment chamber 32. Handle the cuvette assembly 66 by placing the cuvette assembly 66 into the treatment chamber 32 of the device 10, or by the standoffs or flexible tubing of the cuvette assembly 66. Connect a 60 cc syringe, or any other size syringe or the like, to the cuvette assembly 66 and prime the cuvette assembly 66 with 30 cc of heparinized saline 240, in this exemplary implementation. Connect to the patient, activate the light sources 242 in the device 10, and withdraw the appropriate amount of blood 244, the maximum being 30 cc. Most of the aspirated blood will occupy the space in the triple quartz tubes 65, 74 and 82 of the cuvette assembly 66, thereby receiving the photonic energy. Push back the treated blood, with or without added saline, into the patient and then re-aspirate until the total desired volume is reached 246.

Figure 23:
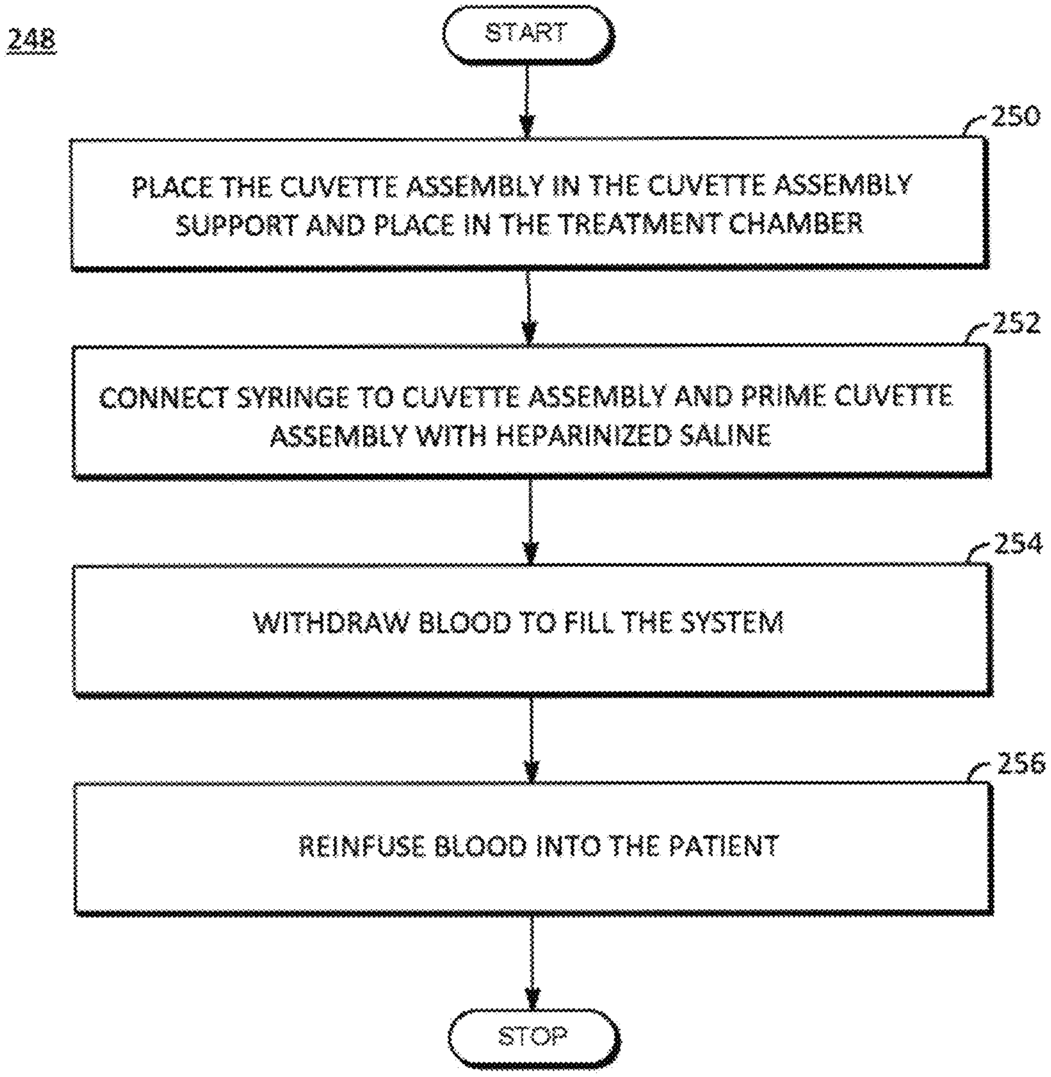
FIG. 23 is a flow diagram of a process for treating blood with the polychromatic phototherapy device using a third embodiment of a veterinary syringe technique in accordance with implementations of this disclosure.

FIG. 23 is a flow diagram showing a process 248 for treating blood using the polychromatic phototherapy device 10 in accordance with an implementation of this disclosure. Process 248 uses a third embodiment of a veterinary syringe technique, and uses a sterilized cuvette assembly 66. Do not use a filter of any kind as it may restrict blood flow. Connect the tubing set to cuvette assembly 66 using sterile technique creating a closed system. Care must be taken not to touch the surface of the cuvette assembly 66 quartz tubes, as fingerprints will impede penetration of the UV sources. If fingerprints or body oils are inadvertently left on the cuvette assembly 66 surface, wipe off with plain alcohol. The cuvette assembly 66 is placed in the treatment chamber 32 in the device 10, 250, taking care to be certain that cuvette assembly 66 is resting on reflective tray 142 (FIG. 21) of the treatment chamber 32. Handle the cuvette assembly 66 by placing the holder 14 with the cuvette assembly 66 into the treatment chamber 32 of the device 10, or by the standoffs or flexible tubing of the cuvette assembly 66. Connect a 60 cc syringe, or any other size syringe or the like, to the cuvette assembly 66 and fill with heparin saline solution 604. Withdraw blood 606 to fill the cuvette assembly 66, clamp off the line to the patient and insert a needle connected to another 60 cc syringe, or any other size syringe or the like, into the port provided by the cannula and/or needle placed into the patient's vein from which blood is withdrawn and then reinfused, and pull the blood through the cuvette assembly 66 into the syringe. Then reverse direction and pull back into the first syringe. Repeat as desired. To terminate the treatment, reinfuse into the patient 256 and if necessary add saline to the first syringe to reinfuse all treated blood into the patient. A female to female Leur lock adapter may also be used to connect two syringes and run the blood back and forth through the cuvette assembly 66.

Any of these above-described treatment techniques with the polychromatic phototherapy device 10 can be used after the administration of an optional liposomal methylene blue treatment with photodynamic therapy. The photodynamic therapy treatment may also be administered during or after treatment with the polychromatic phototherapy device 10. When using liposomal methylene blue, the solution contains two different minerals in an un-bonded and non-oxidized state, their particle size ranges in size from 15 nanometers to 100 nanometers. One is conductive in nature and the other is not, and because of their size they can integrate with cell surface markers and also effect the cell at an intracellular level. The liposomal component is the lipid part of the solution and consists mainly of phosphatidylcholine. Methylene blue is administered through injection (e.g., IV, intramuscular) for active contagions and orally (e.g., sublingually) for prevention. First the methylene blue coats the nanoized minerals and then the lipid component creates the final liposomal solution, which uses ultrasound in a three part process.

When the lipospheres become coupled and are exposed to electromagnetic energy (light), some of this energy can be absorbed and transferred to and enhance the effect of the methylene blue. The energy that is introduced into the lipospheres acts as an energy transfer medium at the cell surface level. The methylene blue can act as an oxidizing agent, at which time it becomes very anti-pathogenic and will quickly deactivate viral and/or bacterial particles. Also, the methylene blue can act as an electron transfer agent within the mitochondria and/or as an electron donor within the Krebs Cycle focusing on Complex 1 and Complex 2, thus enhancing energy by assisting ATP production. The methylene blue can also affect the $Fe^{++}$ on the heme within the RBC's which helps support and enhance the delivery of oxygen to the tissues.

The procedure for administration of liposomal methylene blue includes the following steps: withdraw 0.5 to 1 cc of solution and put in an ounce or two of water. Have the patient take small sips, holding each sip sublingually for as long as possible, at least a few minutes, then swallow. Do this approximately 20 minutes prior to treatment with the device 10 to enable the methylene blue to be absorbed internally.

As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, "X includes at least one of A and B" is intended to mean any of the natural inclusive permutations. That is, if X includes A; X includes B; or X includes both A and B, then "X includes at least one of A and B" is satisfied under any of the foregoing instances. The articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same embodiment, aspect or implementation unless described as such.

While the present disclosure has been described in connection with certain embodiments and measurements, it is to be understood that the present disclosure is not to be limited to the disclosed embodiments and measurements but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for the polychromatic phototherapy treatment of blood, comprising the steps of:

a. preparing a patient for the withdrawal of blood from the patient and for the refusion of blood back into the patient;

b. determining an amount of blood to be treated;

c. initiating the circulatory flow of the determined amount of blood from the patient and back into the patient;

d. treating the blood by exposing the blood flowing in a cuvette assembly to a dual wavelength UVA light source, a UVC light source, at least one dual wavelength red LED light source, at least one amber LED light source, a green LED light source, and a blue LED light source;

e. reinfusing the treated blood into the patient.

2. The method of claim 1, further comprising:

infusing heparin into a container to create a saline/heparin solution and priming the cuvette assembly with the solution;

placing a cannula into a vein of the patient;

dripping a portion of the saline/heparin solution into the patient;

attaching a syringe to an input end of the cuvette assembly;

withdrawing, using the syringe, blood from the patient;

treating the blood by passing the blood through the cuvette assembly while the blood passing through the cuvette assembly is exposed to the dual wavelength UVA light and UVC light, and dual wavelengths of red LED light, amber LED light, green LED light and blue LED light are focused upon selected portions of the cuvette assembly.

3. The method of claim 1, further comprising:

infusing heparin into a container to create a saline/heparin solution and priming the cuvette assembly with the solution;

placing a cannula into a vein of the patient, dripping a portion of the saline/heparin solution into the patient;

lowering the container of saline/heparin solution below the site of the cannula;

aspirating blood from the patient into the cuvette assembly;

treating the blood by passing the blood through the cuvette assembly while the blood passing through the cuvette assembly is exposed to the dual wavelength UVA light and UVC light, and dual wavelengths of red LED light, amber LED light, green LED light and blue LED light are focused upon selected portions of the cuvette assembly; and reinfusing the blood into the patient at a preselected drip rate of at least 10 cc per minute.

4. The method of claim 1, further comprising:

providing one of a multipass Zotsmann and a Hermann hyperbaric ozone technique machine;

connecting the leads of the cuvette assembly with the leads of the one Zotsmann and Hermann machine;

placing a cannula into a vein of the patient, aspirating, using the one of the Zotsmann and Hermann machine, blood from the patient into the cuvette assembly;

treating the blood by passing the blood through the cuvette assembly while the blood passing through the cuvette assembly is exposed to the dual wavelength UVA light and UVC light, and dual wavelengths of red LED light, amber LED light, green LED light and blue LED light are focused upon selected portions of the cuvette assembly.

5. The method of claim 1, further comprising:

filling a syringe with a predetermined amount of saline and blood thinner; and withdrawing the treated blood into the syringe prior to reinfusing the treated blood into the patient.

6. The method of claim 1, further comprising:

connecting a syringe containing heparinized saline solution to the cuvette assembly, the cuvette assembly disposed adjacent the dual wavelength UVA, UVC, dual wavelength red, amber, green and blue LED light sources;

priming the cuvette assembly with the heparinized saline solution;

withdrawing a predetermined amount of treated blood from the cuvette assembly after passing the blood through the cuvette assembly;

reinfusing the predetermined amount of treated blood back into the patient by one of including added saline and a lack of added saline.

7. The method of claim 6, further including:

withdrawing blood from the patient in a quantity to fill the cuvette assembly with blood;

filling the cuvette assembly with the withdrawn quantity of blood; and reinfusing the treated blood and the heparinized saline solution back onto the patient.

8. The method of claim 1, further including the steps of:

collecting a first pass of blood after passing the blood adjacent to the light sources; and conveying the blood in a second pass adjacent the light sources prior to reinfusing the blood into the patient.

* * * * *